(12) United States Patent
Ghiron et al.

(10) Patent No.: US 11,819,706 B2
(45) Date of Patent: *Nov. 21, 2023

(54) MONITORING AND DETECTING MAGNETIC STIMULATION

(71) Applicant: Neuronetics, Inc., Malvern, PA (US)

(72) Inventors: Kenneth Marc Ghiron, Malvern, PA (US); Ian Maxwell Shipway, Bryn Mawr, PA (US); Mark Edward Riehl, Doylestown, PA (US); Ravi Pillutla, Audubon, PA (US)

(73) Assignee: Neuronetics, Inc., Malvern, PA (US)

( * ) Notice: Subject to any disclaimer, the term of this patent is extended or adjusted under 35 U.S.C. 154(b) by 290 days.

This patent is subject to a terminal disclaimer.

(21) Appl. No.: 17/208,828

(22) Filed: Mar. 22, 2021

(65) Prior Publication Data
US 2021/0205631 A1 Jul. 8, 2021

Related U.S. Application Data

(63) Continuation of application No. 16/215,356, filed on Dec. 10, 2018, now Pat. No. 10,981,015, which is a continuation of application No. 14/076,975, filed on Nov. 11, 2013, now Pat. No. 10,183,172.

(51) Int. Cl.
A61N 2/00 (2006.01)
A61N 2/02 (2006.01)
G01R 33/02 (2006.01)

(52) U.S. Cl.
CPC .............. *A61N 2/006* (2013.01); *A61N 2/02* (2013.01); *G01R 33/02* (2013.01)

(58) Field of Classification Search
CPC .................................................. A61N 2/00–12
See application file for complete search history.

(56) References Cited

U.S. PATENT DOCUMENTS

| 5,058,582 A | 10/1991 | Thaler |
| 5,192,263 A | 3/1993 | Kraus et al. |
| 5,441,495 A | 8/1995 | Liboff et al. |
| 6,169,963 B1 | 1/2001 | Markov |

(Continued)

FOREIGN PATENT DOCUMENTS

| CA | 2295134 A1 | 7/1999 |
| JP | 0767972 A | 3/1995 |

(Continued)

*Primary Examiner* — Thaddeus B Cox
(74) *Attorney, Agent, or Firm* — Flaster Greenberg P.C.

(57) ABSTRACT

A method, system, and apparatus for monitoring a magnetic field related to magnetic stimulation may be provided. A system for monitoring a pulsing magnetic field related to magnetic stimulation therapy may include a magnetic stimulation component, a sensor, and a processor. The magnetic stimulation component may be configured to generate the pulsing magnetic field for the magnetic stimulation therapy. The sensor may be configured to generate a signal associated with the pulsing magnetic field. The processor may be configured to estimate a first characteristic associated with a first peak of the signal, estimate a second characteristic associated with a second peak of the signal, and determine a third characteristic of the signal based on the first characteristic and the second characteristic. The processor may be configured to determine whether a failure occurred based on the third characteristic of the signal.

26 Claims, 9 Drawing Sheets

(56) References Cited

U.S. PATENT DOCUMENTS

| | | |
|---|---|---|
| 6,561,968 B1 | 5/2003 | Dissing et al. |
| 7,422,555 B2 | 9/2008 | Zabara |
| 7,601,115 B2 | 10/2009 | Riehl |
| 8,376,925 B1 | 2/2013 | Dennis et al. |
| 2003/0073899 A1 | 4/2003 | Ruohonen et al. |
| 2007/0078292 A1 | 4/2007 | Markov et al. |
| 2007/0142886 A1 | 6/2007 | Fischell et al. |
| 2007/0213783 A1 | 9/2007 | Pless |
| 2008/0287730 A1 | 11/2008 | Spiegel et al. |
| 2009/0105520 A1 | 4/2009 | Sotiriou et al. |
| 2012/0157752 A1 | 6/2012 | Nishikawa et al. |
| 2013/0137918 A1 | 5/2013 | Phillips et al. |
| 2013/0335069 A1 | 12/2013 | Vig et al. |
| 2014/0266176 A1 | 9/2014 | Fernandez et al. |
| 2015/0018692 A1 | 1/2015 | Neuvonen et al. |
| 2015/0133717 A1 | 5/2015 | Pillutla et al. |

FOREIGN PATENT DOCUMENTS

| | | |
|---|---|---|
| JP | H1012549 A | 1/1998 |
| JP | 2007526798 A | 9/2007 |
| JP | 2008500100 A | 1/2008 |
| JP | 2008237692 A | 10/2008 |
| WO | 2008051790 A2 | 5/2008 |
| WO | 2008070001 A2 | 6/2008 |
| WO | 2010147064 A1 | 12/2010 |

MONITORING AND DETECTING MAGNETIC STIMULATION

CROSS REFERENCE TO RELATED APPLICATIONS

This application is a continuation of U.S. patent application Ser. No. 16/215,356, filed Dec. 10, 2018, which issued as U.S. Pat. No. 10,981,015, on Apr. 20, 2021, which is a continuation of U.S. patent application Ser. No. 14/076,975, filed Nov. 11, 2013, which issued as U.S. Pat. No. 10,183,172, on Jan. 22, 2019, all of which are incorporated herein by reference in their entireties.

BACKGROUND

A number of medical ailments may be treated and/or diagnosed through the application of a magnetic field to an afflicted portion of a patient's body. Neurons and muscle cells may be a form of biological circuitry that carry electrical signals and respond to electromagnetic stimuli. When a conductive wire loop is passed through a magnetic field or is in the presence of a changing magnetic field, an electric current may be induced in the wire. The same principle may hold true for conductive biological tissue. When a changing magnetic field is applied to a portion of the body, neurons may be depolarized and stimulated. Muscles associated with the stimulated neurons may contract as though the neurons were firing by normal causes.

A nerve cell or neuron may be stimulated in a number of ways, for example, transcutaneously via transcranial magnetic stimulation (TMS). TMS may use a rapidly changing magnetic field to induce a current on a nerve cell, without having to cut or penetrate the skin. The nerve may "fire" when a membrane potential within the nerve rises with respect to its normal negative ambient level of approximately −90 mV, for example, depending on the type of nerve, local pH of the surrounding tissue, and/or peripheral nerve stimulation.

A magnetic stimulation component may be used to produce the rapidly changing magnetic field inducing a current on a nerve cell. The magnetic stimulation component may fail or operate improperly during treatment, which may result in improper treatment for the patient. For example, the magnetic component may appear to operate correctly, but actually may be producing magnetic field pulses outside of designed device specifications, potentially resulting in improper diagnosis and/or therapy being administered to the patient. Administering an incorrect magnetic field pulse to a patient can affect the magnetic stimulation diagnosis and/or treatment adversely. For example, the treatment provider may believe that the patient is not responding to the treatment, when in fact the intended treatment is not being administered to the patient. Thus, the treatment provider and/or diagnosing clinician may be led to make treatment decisions based on faulty information.

SUMMARY

A method, system, and apparatus for monitoring a magnetic field related to magnetic stimulation therapy may be provided. A system for monitoring a pulsing magnetic field related to magnetic stimulation therapy may include a magnetic stimulation component, a sensor, and a processor. The magnetic stimulation component may be configured to generate the pulsing magnetic field for the magnetic stimulation therapy.

The sensor may be configured to generate a signal associated with the pulsing magnetic field. The signal may include multiple peaks. The signal may indicate a voltage signal proportional to a change in the pulsing magnetic field, a current signal proportional to a change in the pulsing magnetic field, and/or the like. The sensor may include one or more of a conductive coil, a loop having a number of turns based on the pulsing magnetic field, a Hall sensor, a magnetoresistive material, a Faraday effect sensor, a Kerr effect sensor, a flux gate sensor, an inductance change element, a nerve tissue response measurement device, an electric field sensor in a conductive field, or the like.

The processor may be configured to estimate one or more characteristics associated with one or more peaks of the signal. The characteristics may include a voltage of a peak, a current of a peak, a root mean square (RMS) value of a peak, a zero-cross of a peak, a time value of a peak, and/or a time duration of a peak (e.g., a peak duration). The peak(s) may be associated with a single pulse, consecutive pulses, or separate pulses of the pulsing magnetic field.

The processor may be configured to determine one or more characteristics associated with the signal. For example, the processor may determine a decay rate of the signal, a frequency of the signal, a timing associated with the signal, a magnetic flux associated with the signal, and/or a current associated with the signal, for example, based on the estimated characteristic(s). The processor may be configured to determine whether a failure occurred based on the determined characteristic(s) of the signal. The failure may be determined to have occurred when the determined characteristic(s) is outside of a predetermined acceptance window.

The sensor may be configured to generate a voltage induced by a change in the pulsing magnetic field. The processor may be configured to estimate one or more average values of the voltage. An average value may be associated with one or more sets of pulses of the plurality of pulses. The average value(s) may include a weighted average value and/or an unweighted average value. The processor may be configured to determine whether a failure occurred based on the average value(s).

DETAILED DESCRIPTION

Figure 1:
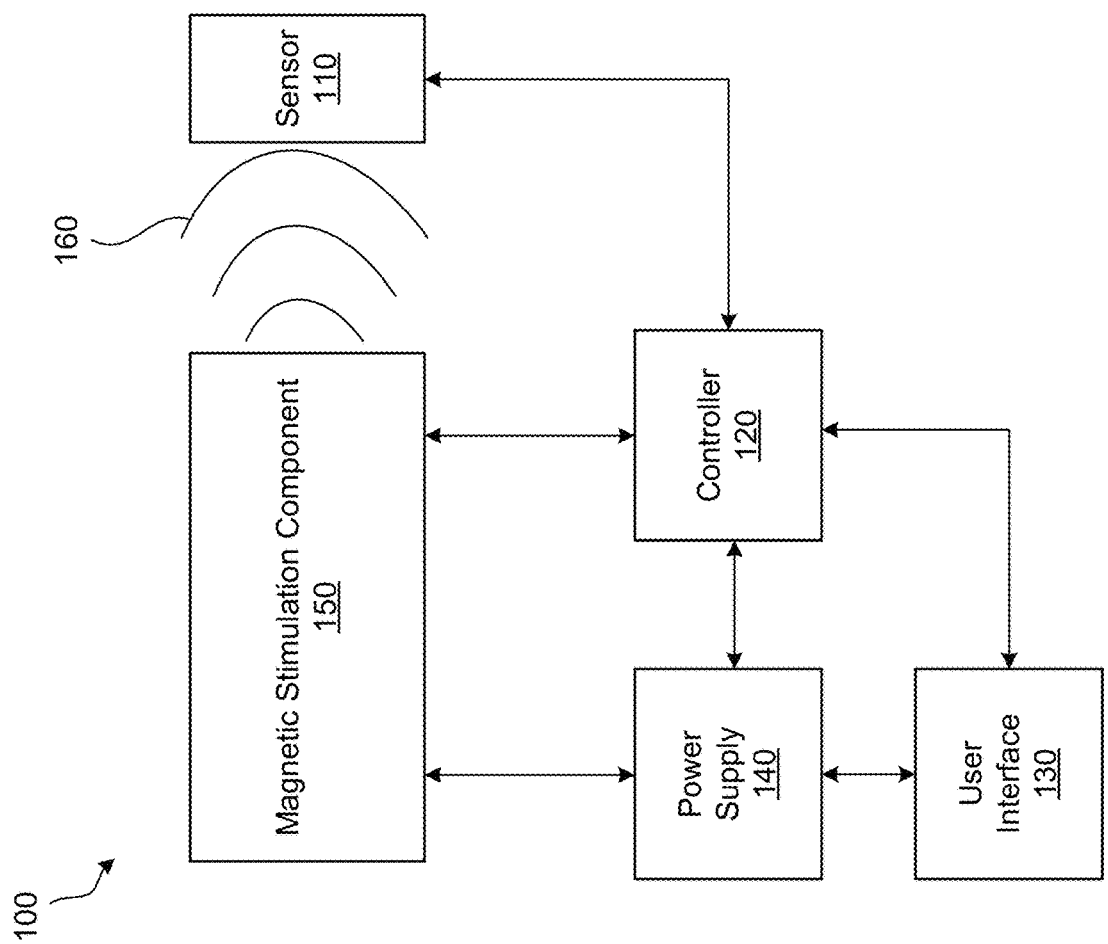
FIG. 1 is a block diagram illustrating an example of a magnetic stimulation system.

A system may be provided that monitors a pulsing magnetic field related to magnetic stimulation therapy, for example, to determine whether or not a system failure has occurred. The system may comprise a magnetic stimulation component, a sensor, and a processor. The magnetic stimulation component may be configured to generate a pulsing magnetic field for performing magnetic stimulation therapy on a patient. The sensor may be configured to generate a signal associated with the pulsing magnetic field of the magnetic stimulation component. For example, the sensor may be placed between the magnetic stimulation component and the patient. In response to the pulsing magnetic field, a current signal, a voltage signal, or the like may be generated in the sensor that may be proportional to the pulsing magnetic field.

The processor may be configured to estimate one or more characteristics (e.g., two characteristics) associated with the signal (e.g., the generated signal) and determine, based on the estimated characteristics, a characteristic of the signal. The processor may be configured to determine whether a failure has occurred based on the determined characteristic of the signal. As such, the system may be able to detect whether the pulsing magnetic field is properly providing magnetic stimulation therapy to the patient. Upon detecting a failure, the system may be configured to pause the TMS procedure, shut down the magnetic stimulation system, alert a user of the magnetic stimulation system, and/or alter a current applied to the magnetic stimulation component.

In 1831, Michael Faraday discovered that the magnitude of an electric field induced on a conductor is proportional to the rate of change of magnetic flux that cuts across the conductor. Faraday's law, well known to those skilled in the art, may be represented as E~−(A*dB/dt), where E is the induced electric field in volts/meter and dB/dt is the time rate of change of magnetic flux density in Tesla/second. In other words, the amount of electric field induced in an object, such as a conductor, may be determined using two factors: the magnetic flux density and the time rate of change of the flux. The greater the flux density and its derivative, the greater the induced electric field and resulting current density. Magnetic flux may be a function of distance. For example, because the magnetic flux density may decrease in strength with relation to the distance from the source of the magnetic field (e.g., $1/r^3$, $1/r^5$, or the like), the flux density may be greater the closer the conductor is to the source of the magnetic field. When the conductor is a coil, the current induced in the coil by the electric field may be increased in proportion to the number of turns of the coil.

An overview of an example operation and application of a magnetic system in which aspects of the various embodiments may be implemented may be provided. The magnitude of an electric field induced on a conductor may be proportional to the rate of change of magnetic flux density across the conductor. When an electric field is induced in a conductor, the electric field may create a corresponding current flow in the conductor. The current flow may be in the same direction of the electric field vector at a given point. The peak electric field may occur when the time rate of change of the magnetic flux density is the greatest and may diminish at other times. During a magnetic pulse, the current may flow in a direction that tends to preserve the magnetic field (e.g., Lenz's Law).

Certain parts of the anatomy (e.g., nerves, tissue, muscle, brain) may act as a conductor and may carry electric current when an pulsed magnetic field is applied. The pulsed magnetic field may be applied to these parts of the anatomy transcutaneously. For example, in the context of TMS, a time-varying magnetic field may be applied across the skull to create an electric field in the brain tissue, which may produce a current. If the induced current is of sufficient density and/or duration, neuron action potential may be reduced to the extent that the membrane sodium channels open and an action potential response is created. An impulse of current may be propagated along the axon membrane that transmits information to other neurons via modulation of neurotransmitters. Such magnetic stimulation may acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations, metabolism, and/or nerve changes to stimulation thresholds, for example, such that depression may be alleviated.

Non-cortical neurons (e.g., cranial nerves, peripheral nerves, sensory nerves) may be stimulated by an induced electric field. For example, peripheral nerves may be intentionally stimulated to diagnose neuropathologies, for example, by observing response times and conduction velocities in response to a pulsed magnetic field induced stimulus. Discomfort and/or pain may result if the induced electric field applied to a peripheral and/or cranial nerve is very intense, and/or focused on a small area of the nerve. This discomfort may be diminished, for example, by intentionally over-stimulating the sensory nerves in the affected nerve bundle so that they can no longer respond to external pain stimuli, or by reducing the intensity and/or focus of the induced electric field that is causing the pain sensation.

Transcutaneous magnetic stimulation may not be limited to treatment of depression. Transcutaneous magnetic stimulation may be used to treat a patient, such as a human, for example, suffering from epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (e.g., panic disorder with and without agoraphobia, social phobia also known as social anxiety disorder, acute stress disorder and/or generalized anxiety disorder), post-traumatic stress disorder (one of the anxiety disorders in DSM), obsessive compulsive disorder (e.g., one of the anxiety disorders in DSM), pain (such as, for example, migraine and trigeminal neuralgia, as well as chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (e.g., dependence, abuse and withdrawal diagnoses for alcohol, cocaine, amphetamine, caffeine, nicotine, *cannabis* and the like), spinal cord injury and regeneration/rehabilitation, stroke, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, autism spectrum disorders, and/or eating disorders (such as bulimia, anorexia and binge eating).

A device may take advantage of the above principles to induce an electric field used in a variety of applications. For example, a magnetic device may be used for electrical stimulation of the anatomy. While the discussion herein focuses on magnetic devices that are used in connection with magnetic stimulation of anatomical tissue, a magnetic device may be utilized in any field of endeavor.

A ferromagnetic core may be used in connection with a magnetic device to produce a magnetic field. For example, a ferromagnetic core may include an arc-shaped (e.g., approximately hemispherical) magnetic material. A ferromagnetic core may include a highly saturable magnetic material having a magnetic saturation of at least 0.5 Tesla. A ferromagnetic core may be shaped to optimize the magnetic field distribution in the treatment area. For example, such a magnetic field may be for purposes of carrying out transcutaneous magnetic stimulation such as, for example, Transcranial Magnetic Stimulation (TMS), Repetitive TMS (rTMS), Magnetic Seizure Therapy (MST), deep TMS (dTMS), controlled and/or varied pulse shape TMS (cTMS), reduction of peripheral nerve discomfort, etc. Although examples described herein may be discussed in connection with TMS and rTMS, the examples described herein may be utilized in connection with any type of magnetic stimulation, such as transcutaneous magnetic stimulation, for example. Furthermore, the embodiments presented herein are not limited to the use of ferromagnetic core magnetic stimulation systems, as other core materials may be used such as, for example, an air core.

FIG. 1 is a block diagram illustrating an example of a magnetic stimulation system. A magnetic stimulation system 100 may comprise a sensor 110, a controller 120, a user interface 130, a power supply 140, and a magnetic stimulation component 150. A magnetic stimulation device may refer to one or more components of a magnetic stimulation system (e.g., the magnetic stimulation system 100).

The magnetic stimulation component 150 may be configured to generate a pulsing magnetic field 160 to conduct magnetic stimulation therapy on a treatment area of a patient. The magnetic stimulation therapy may be, for example, transcranial magnetic stimulation (TMS). TMS may refer to TMS, repetitive transcranial magnetic stimulation (rTMS), deep TMS (dTMS), cTMS, or the like. The magnetic stimulation component 150 may be a treatment coil. The magnetic stimulation component 150 may include a single treatment coil, multiple treatment coils and/or an array of treatment coils. The treatment area may be the prefrontal cortex, for example. The magnetic stimulation component 150 may or may not include a core, such as a magnetic core (e.g., ferromagnetic core), for example. The pulsing magnetic field 160 may include one or more pulse bursts. A pulse burst (e.g., each pulse burst) of the pulsing magnetic field 160 may include one or more pulses.

The sensor 110 may be configured to generate a signal associated with a pulsing magnetic field 160. The sensor 110 may be placed between the magnetic stimulation component 150 and a treatment area of a patient. The sensor 110 may be configured to generate a signal associated with the pulsing magnetic field 160 of the magnetic stimulation component 150 (e.g., a signal induced by the pulsing magnetic field 160). For example, the sensor 110 may convert a physical property (e.g., the strength of pulsing magnetic field 160) into a corresponding electrical signal (e.g., a current signal or a voltage signal). As such, the sensor 110 may detect and/or measure a physical parameter of the pulsing magnetic field and generate a signal associated with the pulsing magnetic field using the detected/measured physical parameter. The generated signal may be a voltage signal, a current signal, and/or the like that may be proportional to a change in the pulsing magnetic field 160. For example, a current may be generated in the sensor 110 that may be proportional to the pulsing magnetic field 160. The sensor 110 may generate a voltage that may be proportional to the magnetic flux density (dB/dt) of the pulsing magnetic field 160.

The sensor 110 may include one or more of a conductive coil, a loop (e.g., having a number of turns based on the pulsing magnetic field), a Hall sensor, a magnetoresistive material, a Faraday effect sensor, a Kerr effect sensor, a flux gate sensor, an inductance change element, a nerve tissue response measurement device, an electric field sensor (e.g., in a conductive field), and/or the like. The sensor 110 may be configured to generate more than one signal, for example, more than one signal that is associated with the pulsing magnetic field 160 generated by the magnetic stimulation component 150.

The controller 120 may be any type of hardware, software, or combination thereof. The controller 120 may be configured to control one or more of the components of the magnetic stimulation system 100, such as the sensor 110, the user interface 130, the power supply 140, and/or the magnetic stimulation component 150, for example to conduct magnetic stimulation therapy. For example, the controller 120 may include a general purpose processor, a special purpose processor, a conventional processor, a digital signal processor (DSP), a plurality of microprocessors, one or more microprocessors in association with a DSP core, a microcontroller, any other type of integrated circuit (IC), a state machine, and/or the like.

The controller 120 may be configured to receive inputs from the user interface 130 and/or the sensor 110 to conduct magnetic stimulation therapy accordingly. For example, the controller 120 may perform signal coding, data processing, power control, input/output processing, and/or any other functionality that enables the controller 120 to operate the magnetic stimulation component for magnetic stimulation. Although the controller 120 of the magnetic stimulation system 100 may be configured to control both the magnetic stimulation component 150 and the sensor, the magnetic stimulation system 100 may include two or more controllers for individually controlling two or more of the components of the magnetic stimulation system 100.

The controller 120 may be configured to estimate (e.g., measure) characteristics associated with the signal generated by the sensor 110 (e.g., associated with one or more peaks of the signal). The controller 120 may estimate a subset of the pulses of the signal or may estimate the signal continuously. By estimating characteristics of the signal, the controller 120 may estimate a model of what is incurring in the brain of a patient in response to the pulsing magnetic field.

As described herein, the controller 120 may be configured to estimate a characteristics associated with the signal generated by the sensor 110. For example, the controller 120 may estimate a voltage associated with the generated signal (e.g., a voltage associated with a peak of the generated signal), a current associated with the generated signal (e.g., a current associated with a peak of the generated signal), a Root Mean Square (RMS) value associated with the generated signal (e.g., a RMS value associated with a peak of the generated signal), a zero-cross time associated with the generated signal (e.g., a zero-cross time associated with a peak of the generated signal), a time value associated with the generated signal (e.g., a time value associated with a peak of the generated signal), and/or a time duration of the generated signal (e.g., a time duration associated with a peak of the generated signal, for example, peak duration). For example, the peak duration may be characterized by a time duration between an initial rising edge of a peak and a first zero-crossing of the peak.

The controller 120 may determine one or more characteristics associated with the signal generated by the sensor 110. For example, the controller 120 may determine characteristic(s) associated with the signal using one or more estimated characteristics of the signal. As described herein, the controller 120 may determine a decay rate of the generated signal, a frequency of the generated signal, a timing associated with the generated signal, a magnetic flux associated with the generated signal, a pulse shape of the generated signal, a voltage associated with the generated signal, and/or a current associated with the generated signal.

The pulsing magnetic field 160 may be characterized by one or more pulse bursts. A pulse burst may be characterized by one or more pulses. Characteristics associated with the signal generated by the sensor 110 may be associated with the same pulse of the pulsing magnetic field 160 or different pulses of the pulsing magnetic field 160. The characteristics associated with the generated signal may be associated with the same pulse burst of the pulsing magnetic field 160 or different pulse bursts of the pulsing magnetic field 160.

The controller 120 may determine whether a failure has occurred based on one or more characteristics of the signal generated by the sensor 110. For example, the controller 120 may determine whether a failure has occurred based on whether a characteristic of the generated signal (e.g., a determined characteristic) is outside of a predetermined acceptance window. The predetermined acceptance window may be defined based on an expected signal associated with the pulsing magnetic field. The acceptance window may be adjustable based on the settings of the type of magnetic stimulation therapy, the magnetic stimulation treatment parameters, and/or the patient parameters. For example, the controller 120 may receive settings of the magnetic stimulation procedure and compare the settings of the magnetic stimulation procedure with characteristic(s) of the generated signal to determine whether a failure has occurred. For example, the controller 120 may determine that a failure has occurred when a difference between two or more characteristics (e.g., characteristics relating to peaks) of the generated signal exceeds an expected value (e.g., which may be determined based on magnetic stimulation settings). For example, the expected value may include an expected voltage value, an expected current value, and/or the like.

In the event a failure is determined to have occurred, the controller 120 may enter a failure mode. In the failure mode, the controller 120 may pause the magnetic stimulation procedure, shut down the magnetic stimulation component 150, alert a user of the magnetic stimulation system 100, and/or alter a current applied to the magnetic stimulation component 150. For example, when the controller 120 enters the failure mode, the controller 120 may adjust the frequency at which it estimates characteristics of the generated signal. For example, the controller 120 may check for failures more frequently after a first failure is detected.

The controller 120 may log one or more characteristics of the signal generated by the sensor 110 (e.g., estimated characteristics and/or determined characteristics). The controller 120 may be configured to log one or more failures of the magnetic stimulation procedure. In one or more embodiments, the magnetic stimulation system 100 may include an indicator that may indicate to a user of the magnetic stimulation system 100 that a failure has occurred. For example, the indicator may be a light, a speaker, an icon displayed on the user interface 130, and/or the like.

The user interface 130 may be any type of interface in which a user of the magnetic stimulation system 100 may initiate, adjust, and/or end the magnetic stimulation procedure. For example, the user interface may include a personal computer (PC), a keyboard, a mouse, a touchscreen, a wireless device, and/or the like, that allows for an interface between the user and the magnetic stimulation system 100.

The power supply 140 may be any type of power source that provides sufficient energy for the magnetic stimulation component 150 to generate the pulsing magnetic field 160 for its intended purpose, for example, for TMS, rTMS, MST or any other type of application. For example, the power supply 140 may be a conventional 120 or 240 VAC main power source.

Figure 2:
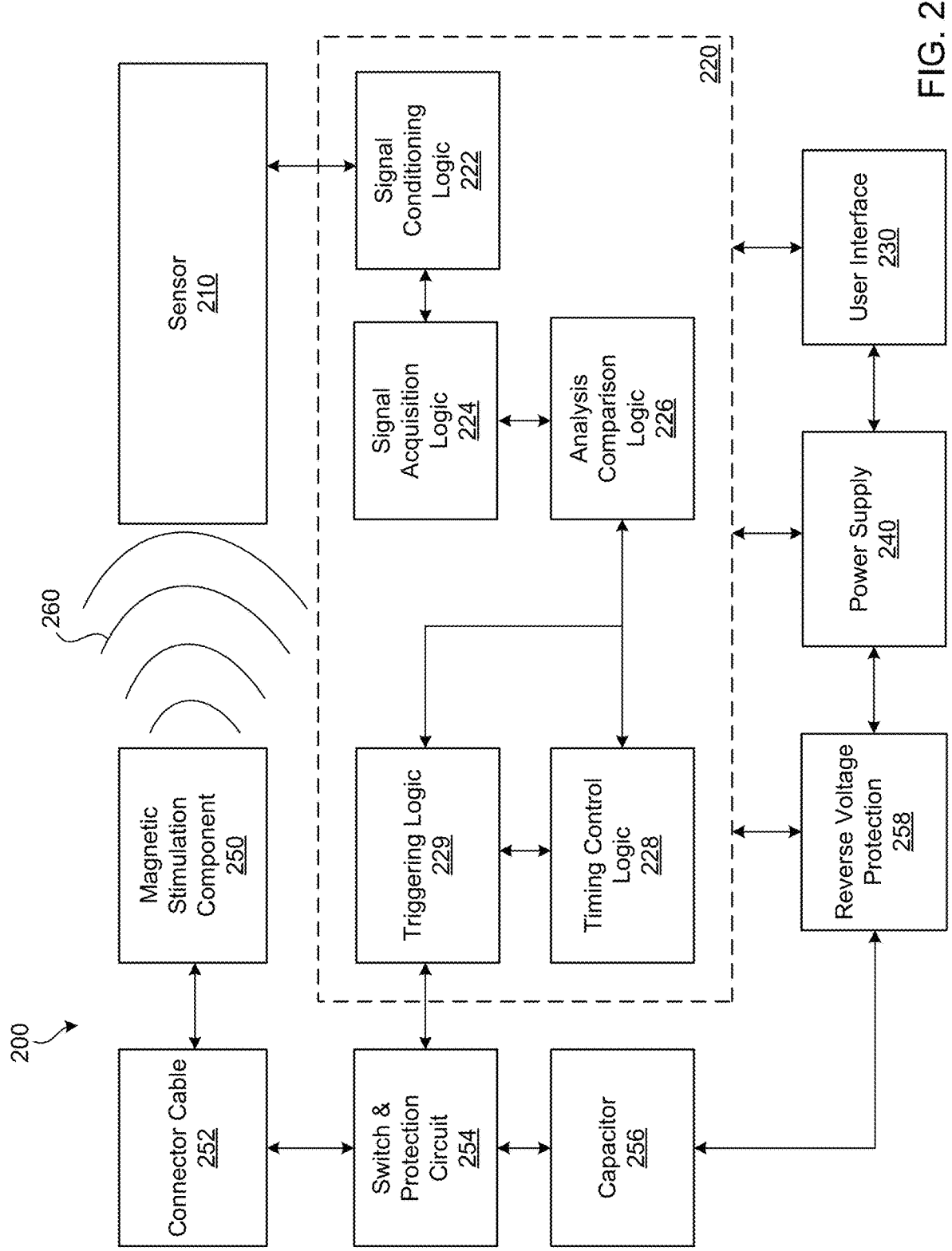
FIG. 2 is a block diagram illustrating an example of a magnetic stimulation system.

FIG. 2 is a block diagram illustrating an example of a magnetic stimulation system. The magnetic stimulation system 200 may comprise a sensor 210, a controller 220, a user interface 230, a power supply 240, a magnetic stimulation component 250, a connector cable 252, a switch and protection circuit 254, a capacitor 256, and reverse voltage protection logic 258. The magnetic stimulation system 200 may be substantially similar to the magnetic stimulation system 100.

The sensor 210 may be substantially similar to the sensor 110 described herein. The sensor 210 may be configured to perform one or more of the functions described herein with reference to the sensor 110. For example, the sensor 210 may be configured to generate a signal associated with a pulsing magnetic field 260.

The magnetic stimulation component 250 may be substantially similar to the magnetic stimulation component 150 described herein. The magnetic stimulation component 250 may be configured to perform one or more of the functions described herein with reference to the magnetic stimulation component 150. For example, the magnetic stimulation component 250 may generate a pulsing magnetic field 260 that may be used to conduct magnetic stimulation therapy on a treatment area of a patient.

The user interface 230 may be substantially similar to the user interface 130 described herein. For example, the user interface 230 may be configured to perform one or more of the functions described herein with reference to the user interface 130. The power supply 240 may be substantially similar to the power supply 140 described herein. For example, the power supply 240 may be configured to perform one or more of the functions described herein with reference to the power supply 140.

The controller 220 may include signal conditioning logic 222, signal acquisition logic 224, analysis comparison logic 226, triggering logic 229, and timing control logic 228. The controller 220 may be substantially similar to the controller 120 described herein. For example, the controller 220 may be configured to perform one or more of the functions described herein with reference to controller 120. The controller 220 may be any type of hardware, software, and/or combination thereof. The controller 220 may be configured to control one or more of the components of the magnetic stimulation system 200. For example, the controller 220 may be configured to estimate and/or determine one or more characteristics associated with the generated signal, and/or the controller 220 may be configured to determine whether a failure has occurred based on a characteristic of the signal generated by the sensor 210.

The controller 220, for example, via the signal conditioning logic 222, may receive a signal from the sensor 210. The signal conditioning logic 222 may manipulate the signal received from the sensor 210 into a format used by the controller 220 for further processing. For example, the signal conditioning logic 222 may filter, amplify, and/or isolate the signal received from the sensor 210. The signal received from the sensor 210 may include a voltage signal, a current signal, or the like that is proportional to the pulsing magnetic field 260.

The signal acquisition logic 224 may receive the generated signal from the signal conditioning logic 222. The signal acquisition logic 224 may sample the signal and/or convert the signal into a digital signal that may be utilized by the controller 220. The signal acquisition logic 224 may include one or more analog-to-digital converters. For example, the signal acquisition logic 224 may receive an analog signal from the signal conditioning logic 222 and may convert the signal into a digital signal for further processing by the controller 220.

The analysis comparison logic 226 may receive the signal from the signal acquisition logic 224. The analysis comparison logic 226 may compare a characteristic of the signal with a setting of the magnetic stimulation system to determine whether a failure has occurred. For example, the setting of the magnetic stimulation system may include one or more expected characteristics of the pulsing magnetic field 260 generated by the magnetic stimulation component 250. The characteristics of the pulsing magnetic field 260 may be specific to the treatment being conducted by the magnetic stimulation system. As such, the analysis comparison logic 226 may analyze whether the magnetic stimulation system (e.g., the magnetic stimulation component 250) is properly providing treatment.

The timing control logic 228 may coordinate the timing of the components of the magnetic stimulation system 200. For example, the timing control logic 228 may coordinate the timing between the magnetic stimulation component 250 and the signal generated by the sensor 210 (e.g., and received via the controller 220). As such, the timing control logic 228 may ensure that the controller 220 is comparing a signal generated by the sensor 210 with a corresponding pulsing magnetic field 260 generated by the magnetic stimulation component 250.

The triggering logic 229 may initiate actions of the magnetic stimulation system 200 when certain events occur. The triggering logic 229 may receive timing information from the timing control logic 228. The triggering logic 229 may determine the timing relationship between a signal generated by the sensor 210 and the pulsing magnetic field 260. For example, the triggering logic 229 may determine whether or not a signal received from the sensor 210 is in response to the pulsing magnetic field 260. The triggering logic 229 may relay this information to the analysis comparison logic 226 so the occurrence of a failure may be determined.

The controller 220 may include more or less than the components illustrated in FIG. 2. For example, the controller 220 may include an edge detection circuit. The edge detection circuit may be configured to measure a start time and an end time of a pulse of the generated signal indicative of the pulsing magnetic field. The controller 220 may include a peak detection circuit. The peak detection circuit may be configured to receive the generated signal (e.g., from the sensor 210) and determine one or more peaks of a pulse(s) of the generated signal. For example, the peak detection circuit may be configured to determine one or more characteristics (e.g., voltage, current, time, etc.) associated with a peak of a pulse(s) of the generated signal.

The connector cable 252 may provide for an electrical connection and/or electrical communication between the magnetic stimulation component 250 and the switch and protection circuit 254. The switch and protection circuit 254 may be any type of electrical switching device that can operate the magnetic stimulation system (e.g., the magnetic stimulation component 250), for example, by switching power from the capacitor 256 and/or the power supply 240 on and off. For example, the switch and protection circuit 254 may be operated to switch power from the power supply 240 to charge the capacitor 256. The switch and protection circuit 254 may be used to discharge the capacitor 256 through the magnetic stimulation component 250, for example, to generate the pulsing magnetic field 260 that may be used for treatment. As such, when the switch and protection circuit 254 activates to produce the pulse in the magnetic stimulation component 250, currents (e.g., peak currents in excess of 1000 A) may be delivered to the magnetic stimulation component 250 from the charge stored on the capacitor 256.

The capacitor 256 may provide energy storage for the magnetic stimulation component 250. The capacitor 256 may include a single capacitor and/or a capacitor bank. The capacitor 256 may include any number and/or type of capacitor(s) that are appropriate for the power level, charging time, and/or pulse type used by the magnetic stimulation system 200. For example, the capacitor 256 may include eight 10 µF capacitors that may be connected in parallel to result in 80 µF of total capacitance. For example, the capacitor 256 may be a single 80 µF capacitor.

The capacitor 256 may be used, for example, in applications where a 120 VAC power source or the like is available (e.g., where only a 120 VAC power source or the like is available). A typical doctor's office may be equipped with a conventional (e.g., 120 VAC or the like) power supply rather than a higher-power 240 VAC or three-phase power supply. The capacitor 256 may be used to produce higher peak currents in the magnetic stimulation component 250 than would be possible by driving the magnetic stimulation component 250 directly from the power supply 240 alone. For example, the power supply 240 may convert 120 VAC at its input to 1500 VDC at its output, with the DC output capable of producing 1 Amp DC at 1500 VDC. Using capacitor 256 may allow for higher peak pulse current to flow into the magnetic stimulation component 250 than the 1 Amp produced by the power supply 240. As such, the capacitor 256 may be charged up to the power supply's 240 output voltage in the time period between pulses that are delivered to the magnetic stimulation component 250. When the switch and protection circuit 254 activates to produce the pulse in the magnetic stimulation component 250, peak currents in excess of 1000 A may be delivered to the magnetic stimulation component 250 from the charge stored on the capacitor 256. The magnitude of this peak current may be dictated by the inductance of the magnetic stimulation component 250, and/or by the capacitance value and/or voltage level stored on the capacitor 256 prior to the pulse. The capacitor 256 may be used regardless of the type of power supply 240 available. For example, the capacitor 256 may be used in situations where the power supply 240 is a 240 VAC or three-phase power supply to, for example, produce desired peak currents for input into the magnetic stimulation component 250.

The reverse voltage protection 258 may include reverse bias protection for the magnetic stimulation system 200 (e.g., for the magnetic stimulation component). For example, the reverse voltage protection 258 may include one or more diodes (e.g., blocking diode, Schottky diode, etc.) and/or a receiver bias protection switch (e.g., PNP transistor, P-Channel FET, etc.).

Figure 3:
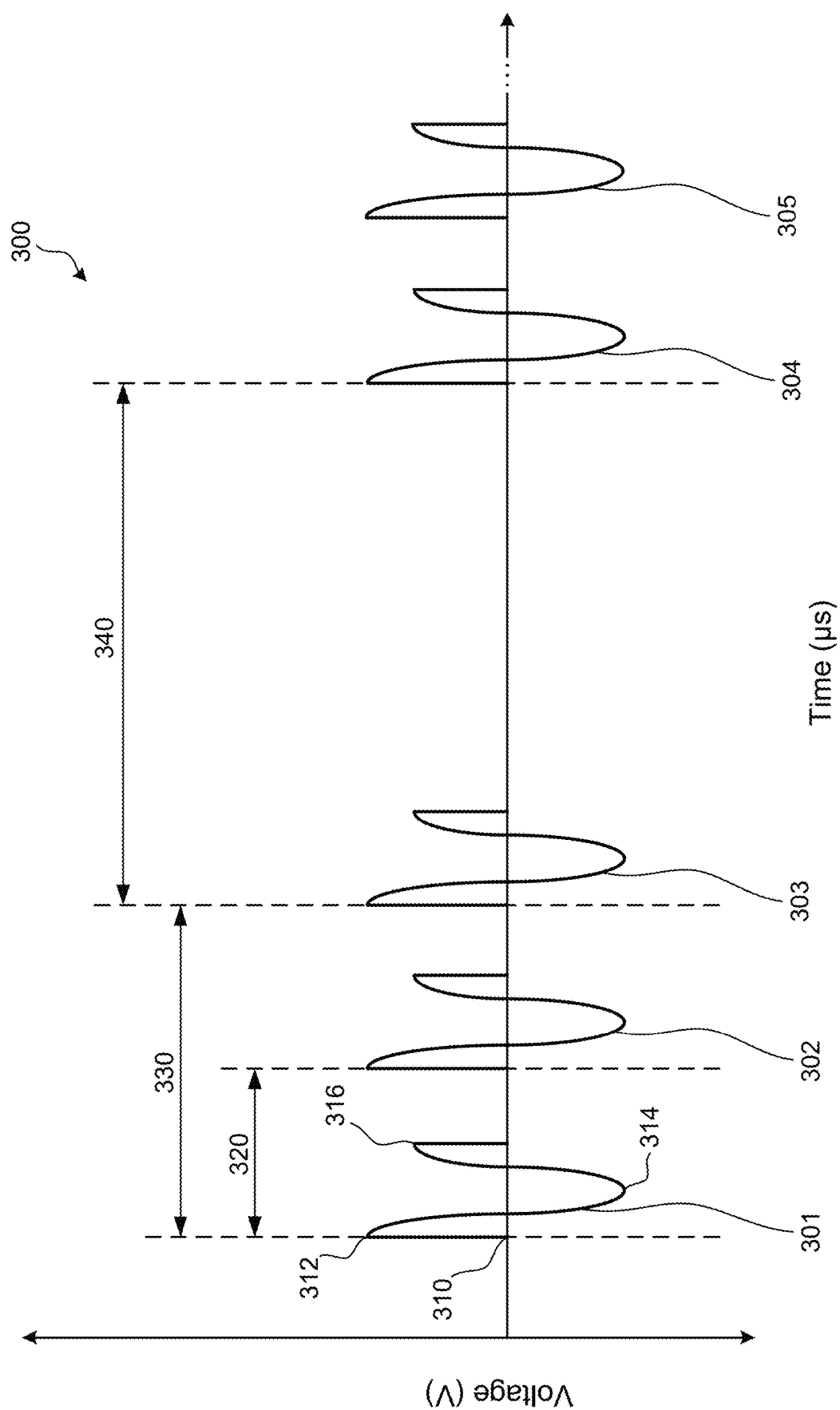
FIG. 3 is a diagram illustrating an example waveform of a signal received by a controller of a magnetic stimulation system.

FIG. 3 is a diagram illustrating an example waveform of a signal received by a magnetic stimulation system (e.g., magnetic stimulation system 100 or magnetic stimulation system 200). As described herein, a controller (e.g., controller 120 or controller 220) may receive a signal from a sensor (e.g., sensor 110 or sensor 210) that may be indicative of a pulsing magnetic field (e.g., pulsing magnetic field 160 or pulsing magnetic field 260) generated by a magnetic stimulation component (e.g., magnetic stimulation component 150 or magnetic stimulation component 250). For example, a current may be generated in the sensor that may be proportional to the pulsing magnetic field. The sensor may generate a voltage that may be proportional to a rate of change of the magnetic flux density (dB/dt) of the pulsing magnetic field. The signal received by the controller may include a voltage signal, such as voltage signal 300. Although described with reference to voltage signal 300, the signal received by the controller from the sensor may be in other units (e.g., a current signal, a power signal, and/or the like).

The magnetic stimulation system may be configured to estimate one or more characteristics associated with the signal generated by the sensor (e.g., generated signal 300), for example, as described herein. The magnetic stimulation system may be configured to determine one or more characteristics associated with the generated signal based on the estimated characteristic(s), for example, as described herein. The estimated and/or determined characteristics of the generated signal may include a pulse repetition rate, pulse interval, stimulation interval, timing of a zero-crossing, a timing of a peak of a pulse, amplitude of a peak, pulse shape, peak to RMS ratio, pulse duration, peak duration, rolling average of one or more pulses, and/or the like, for example, as described herein with reference to voltage signal 300.

The voltage signal 300 may include one or more pulses and one or more pulse bursts. A pulse of the voltage signal may correspond with a pulse of the pulsing magnetic field. A pulse burst may include one or more pulses. The voltage signal 300 may include a first pulse 301, a second pulse 302, a third pulse 303, a fourth pulse 304, and a fifth pulse 305. The first pulse 301, the second pulse 302, and the third pulse 303 may be part of a first pulse burst. The fourth pulse 304 and the fifth pulse 305 may be part of a second pulse burst.

A pulse may include an initial rising edge, a first peak, a second peak, a third peak, and a pulse interval. For example, the first pulse 301 may include an initial rising edge 310, a first peak 312, a second peak 314, a third peak 316, and a pulse interval 320. The initial rising edge of a pulse may be a time when the pulse begins, for example, when the pulse exceeds 0 V. The first peak of the pulse may be characterized by a time and a maximum voltage of the pulse after the initial rising edge and before the pulse decreases back to 0 V. The second peak of the pulse may be characterized by a time and a minimum voltage of the pulse after a zero-crossing after the first peak and before the pulse increases back to 0 V. The third peak of the pulse may be characterized by a time and a second maximum voltage after a zero-crossing after the second peak and before the pulse decreases back to 0 V. After the third peak, the pulse may decrease to 0 V (e.g., after crossing 0 V one or more times, for example, oscillating) and before an initial rising edge of a subsequent pulse.

The pulse interval may be indicative of a time between an initial rising edge of a pulse to an initial rising edge of a subsequent pulse. For example, the pulse interval 320 may be indicative of the time between the initial rising edge 310 of the first pulse 301 to the initial rising edge of the second pulse 302. The stimulation time of a pulse burst may be calculated based on the time between the initial rising edge of a first pulse in the pulse burst to the initial rising edge of the last pulse in the pulse burst. For example, stimulation time 330 may indicate the time duration between the initial rising edge 310 of the first pulse 301 to the initial rising edge of the third pulse 303. For example, the stimulation time 330 may be indicative of the duration of time of a pulse burst of the pulsing magnetic field. The stimulation interval may be indicative of a time between the initial rising edge (e.g., the first peak) of a last pulse in a pulse burst to the initial rising edge (e.g., the first peak) of a first pulse in a subsequent pulse burst. For example, the stimulation interval 340 may be indicative of the time between pulse bursts of a pulsing magnetic field. For example, the stimulation interval 340 may indicate the time between the initial rising edge (e.g., the first peak) of the third pulse 303 (e.g., which may be the last pulse of the first pulse burst) to the initial rising edge (e.g., the first peak) of the fourth pulse 304 (e.g., which may be the first pulse of the second pulse burst).

Figure 4A:
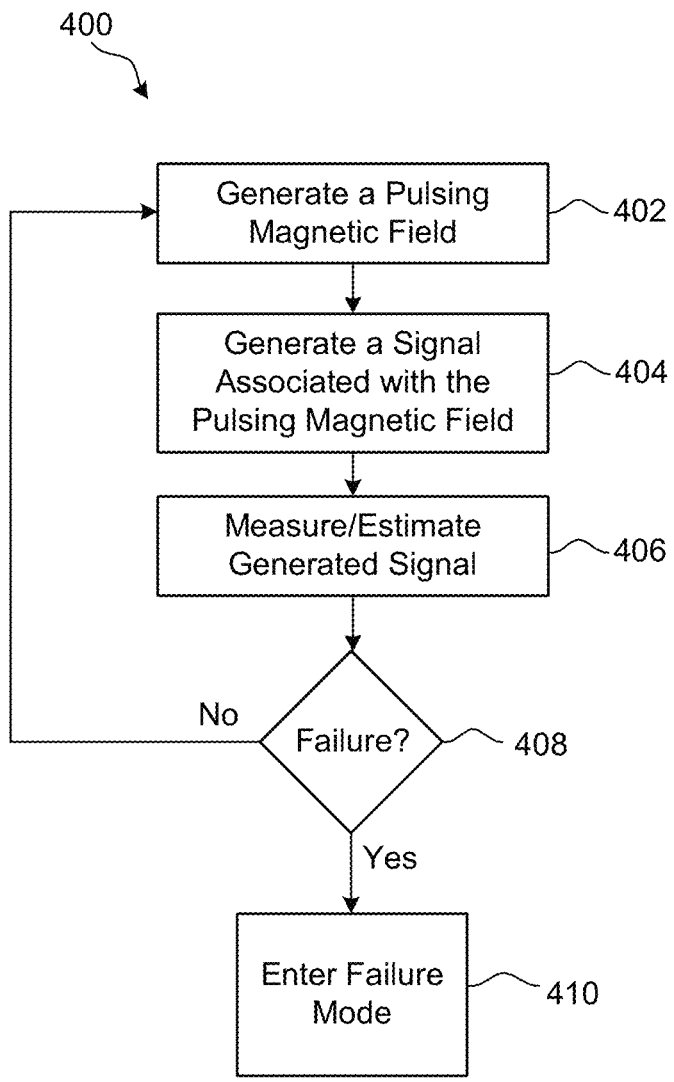
FIG. 4A is a flow diagram illustrating an example procedure for determining whether a failure has occurred.

FIG. 4A is a flow diagram illustrating an example procedure for determining whether a failure has occurred. The procedure 400 may be performed (e.g., partially or entirely) by a magnetic stimulation system, for example, the magnetic stimulation system 100 or the magnetic stimulation system 200, as described herein. For example, the entirety or a subset of the operations described with reference to the procedure 400 may be performed by one or more of the magnetic stimulation systems as described herein. The procedure 400 may be performed before treatment (e.g., for calibration of the magnetic stimulation system), during treatment, and/or after treatment. As such, the procedure 400 may be performed without a patient present.

At 402, a magnetic stimulation system (e.g., a magnetic stimulation component) may generate a pulsing magnetic field. The pulsing magnetic field may be generated for magnetic stimulation treatment, for preparation of magnetic stimulation treatment, to calibrate the system, and/or the like. The pulsing magnetic field may include one or more pulse bursts. A pulse burst may include one or more pulses. The pulse bursts may vary from one another. For example, the pulse bursts may be at different voltage levels, have a different number of pulses per pulse burst, and/or have a different stimulation time. For example, the pulsing magnetic field may pulse approximately 0.1 to 100 pulses per second (pps) (Hz). This may be referred to as the pulse repetition rate. For example, the frequency of a pulse may be approximately 1-10 kHz. For example, the pulsing magnetic field may include approximately ten pulses per second for four seconds, followed by a brief intermission (e.g., which may be repeated). In total, the pulsing magnetic field may include approximately 3,000 pulses over a 37 minute period. The stimulation voltage (e.g., which may refer to the maximum voltage of a pulse) may be approximately 1 V.

At 404, a sensor of the magnetic stimulation system may generate a signal associated with the pulsing magnetic field, for example, as described herein. The generated signal may include one or more peaks. At 406, the magnetic stimulation system (e.g., a controller) may estimate one or more characteristics associated with the generated signal, for example, as described herein. The generated signal may include a voltage signal, for example, that may be proportional to a change in the pulsing magnetic field generated by the magnetic stimulation system. The generated signal may include a current signal, for example, that may be proportional to a change in the pulsing magnetic field generated by the magnetic stimulation system.

The magnetic stimulation system may estimate a characteristic associated with a peak of the generated signal. The generated signal may include one or more pulses, each of which may include one or more peaks. The peak of a generated signal may be any of the peaks described herein, for example, the first peak of a pulse, the second peak of a pulse, or the third peak of a pulse. The first peak of a generated signal (e.g., or second peak, or third peak) may or may not correspond to the first peak of a pulse (e.g., or second peak, or third peak, respectively) of the generated signal. For example, the first peak of a generated signal may refer to the first, second, or third peak of a pulse of the generated signal.

Estimating a characteristic associated with a peak of the generated signal may include measuring the characteristic associated with the peak of the generated signal. The characteristic associated with the peak of the generated signal may include a voltage of the peak, a current of the peak, a root mean square (RMS) value of the peak, a zero-cross of the peak (e.g., a time associated with a zero-cross of a peak), a time value of the peak, a time duration of the peak, and/or the like. The zero-cross of a peak may refer to a time associated with the zero-cross immediately preceding the peak and/or the zero-cross following to the peak.

The magnetic stimulation system may estimate one or more characteristics associated with one or more peaks of the generated signal. The peak(s) of the generated signal may be associated with a single pulse of the pulsing magnetic field generated by the magnetic stimulation system. The peak(s) of the generated signal may be associated with more than one pulse of the pulsing magnetic field. For example, the peak(s) of the generated signal may be associated with one or more pulse bursts of the pulsing magnetic field. The magnetic stimulation system may estimate characteristic(s) of more than one peak of more than one pulse of the pulsing magnetic field.

At 408, it may be determined whether a failure has occurred, for example, as described herein. The magnetic stimulation system may estimate characteristic(s) of the generated signal (e.g., at 406). The magnetic stimulation system may determine characteristic(s) of the generated signal based on the estimated characteristic(s) of the generated signal. For example, a determined characteristic of the generated signal may include a decay rate of the generated signal, a frequency of the generated signal, a timing associated with the generated signal, a magnetic flux associated with the generated signal, a current associated with the generated signal, a voltage associated with the generated signal, and/or a combination thereof.

The magnetic stimulation system may determine whether a failure has occurred based on the determined characteristic(s) of the generated signal. For example, the magnetic stimulation system may determine whether a failure has occurred based on whether a characteristic of the generated signal (e.g., a determined characteristic) is outside of a predetermined acceptance window. The predetermined acceptance window may be set based on an expected signal associated with the pulsing magnetic field. For example, the magnetic stimulation system may be configured with, pre-configured with, and/or configured to receive one or more settings of the magnetic stimulation procedure and compare the setting(s) with one or more characteristics of the generated signal to determine whether a failure has occurred. The magnetic stimulation system may determine that a failure has occurred when a difference between two or more characteristics (e.g., characteristics relating to peaks) of the generated signal exceeds an expected value (e.g., which may be determined based on magnetic stimulation settings). For example, the expected value may be an expected voltage value or an expected current value.

If a failure is determined to have occurred at 408, then the magnetic stimulation system may enter failure mode at 410. In failure mode, the magnetic stimulation system may pause the magnetic stimulation procedure, shut down the magnetic stimulation system, alert a user of the magnetic stimulation system that a failure has occurred, and/or alter a current applied to the magnetic stimulation component. When the magnetic stimulation system enters the failure mode, the magnetic stimulation system may adjust the frequency at which it estimates characteristics of the generated signal. For example, the magnetic stimulation system may check for failures more frequently after a failure is detected. If a failure is determined not to have occurred at 408, then the magnetic stimulation system may continue generating the pulsing magnetic field (e.g., until a magnetic stimulation treatment session is complete, until calibration is complete, and/or the like).

Figure 4B:
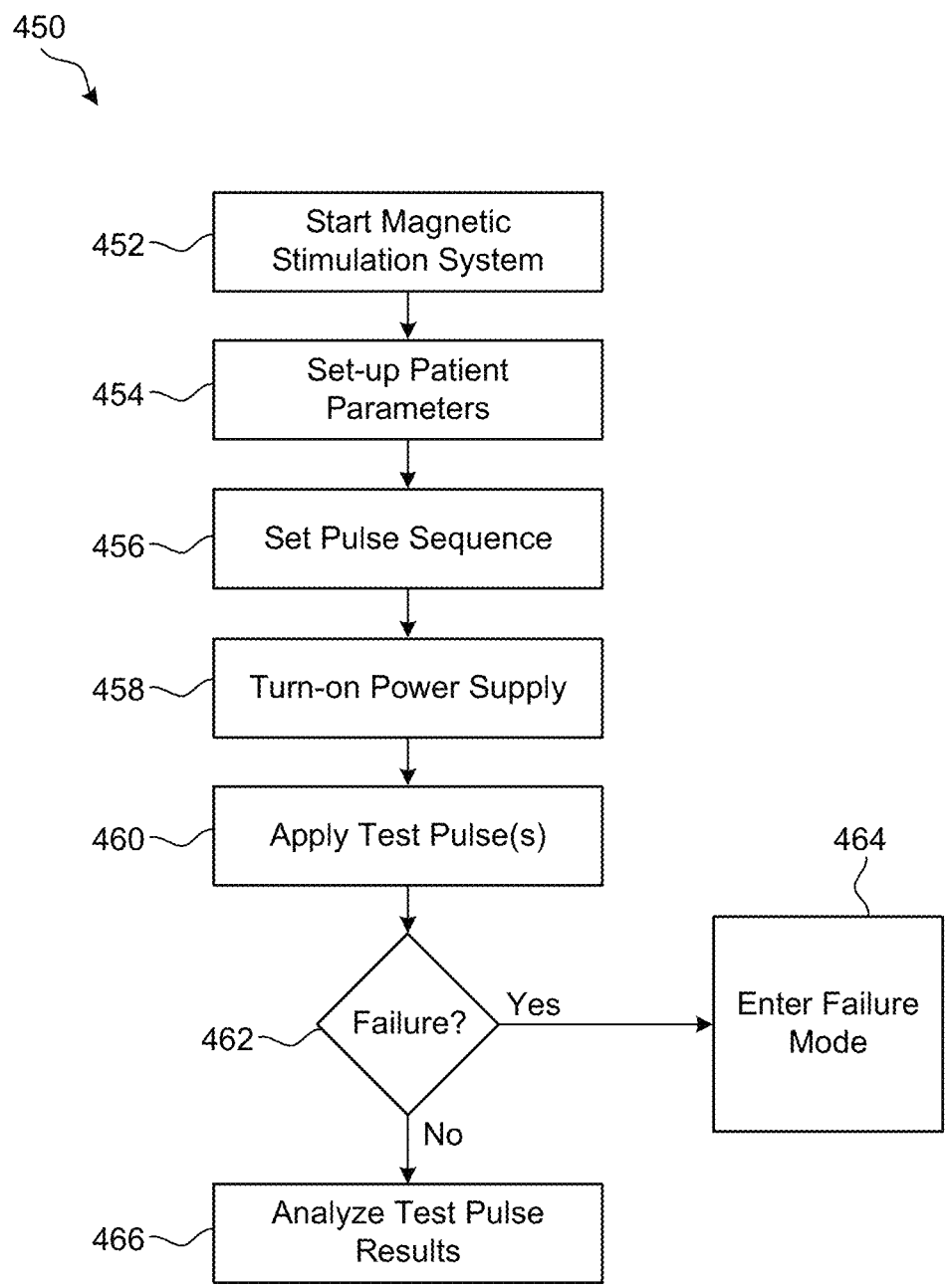
FIG. 4B is a flow diagram illustrating an example procedure for determining whether a failure has occurred.

FIG. 4B is a flow diagram illustrating an example procedure for determining whether a failure has occurred. The procedure 450 may be performed (e.g., partially or entirely) by a magnetic stimulation system, for example, the magnetic stimulation system 100 or the magnetic stimulation system 200, as described herein. For example, the entirety or a subset of the operations described with reference to procedure 450 may be performed by one or more of the magnetic stimulation systems as described herein. The procedure 450 may be performed before treatment (e.g., for calibration of the magnetic stimulation system), during treatment, and/or after treatment. As such, the procedure 450 may be performed without a patient present.

The procedure 450 may begin at 452 when the magnetic stimulation system is started. At 454, the patient parameters may be set-up. The patient parameters may include one or more parameters relating to the patient. For example, the patient parameters may include physical characteristics of the patient, such as height, weight, age, gender, and/or the like, a number of previous treatments the patient has received, a number of treatments the patient is currently receiving, etc. The patient does not have to be present for the procedure 450 to be performed.

At 456, the pulse sequence may be set-up. The pulse sequence parameters may include one or more parameters relating to the magnetic stimulation procedure, such as a duration for the magnetic stimulation procedure, a strength(s) for the magnetic stimulation procedure, a number of pulses and/or pulse bursts of the magnetic stimulation procedure, parameter(s) relating to the pulses and/or pulse bursts of the magnetic stimulation procedure, and/or the like. At 458, the power supply of the magnetic stimulation component may be turned on. This may initialize the magnetic stimulation system for the generation of a pulsing magnetic field.

At 460, one or more test pulses may be generated by the magnetic stimulation system (e.g., the magnetic stimulation component). The test pulses may be utilized to determine whether or not the magnetic stimulation system is working properly before initiating the treatment for the patient. As such, the test pulses may be performed without the magnetic stimulation component and/or the patient in position for treatment. For example, the test pulses may include a total of seven pulses; three pulses at two different voltage levels followed by a clearing pulse. At 462, it may be determined whether a failure has occurred. The determination may be performed by the magnetic stimulation system, for example, as described herein. If a failure is determined to have occurred, then the magnetic stimulation system may enter failure mode at 464. The failure mode may be as described herein.

If a failure is determined not to have occurred, then the test pulse results may be analyzed at 466. The test pulse results may be analyzed to properly configure the magnetic stimulation treatment for the patient. For example, even if a failure is determined not to have occurred at 462, the test pulses may be used to more accurately calibrate the magnetic stimulation treatment for the patient.

After 466, the procedure 450 may include one or more of the processes described with reference to procedure 400. The procedure 450 may be a precursor to magnetic stimulation therapy, and as such, after 466 magnetic stimulation treatment may begin on a patient (e.g., the patient whose parameters were used in 454), for example, according to procedure 400.

Figure 5:
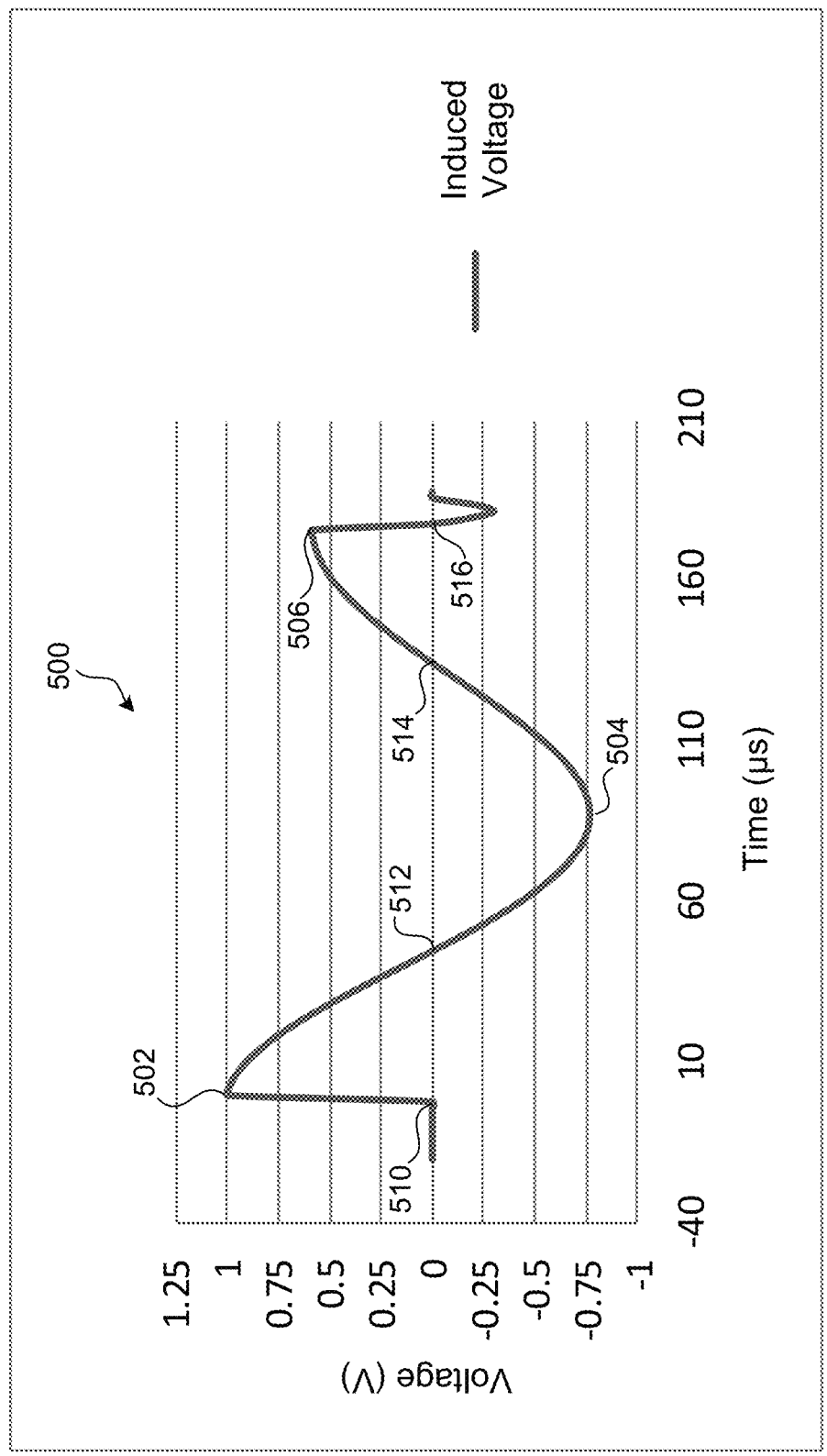
FIG. 5 is a diagram illustrating an example signal of an expected voltage induced on a sensor.
Figure 6:
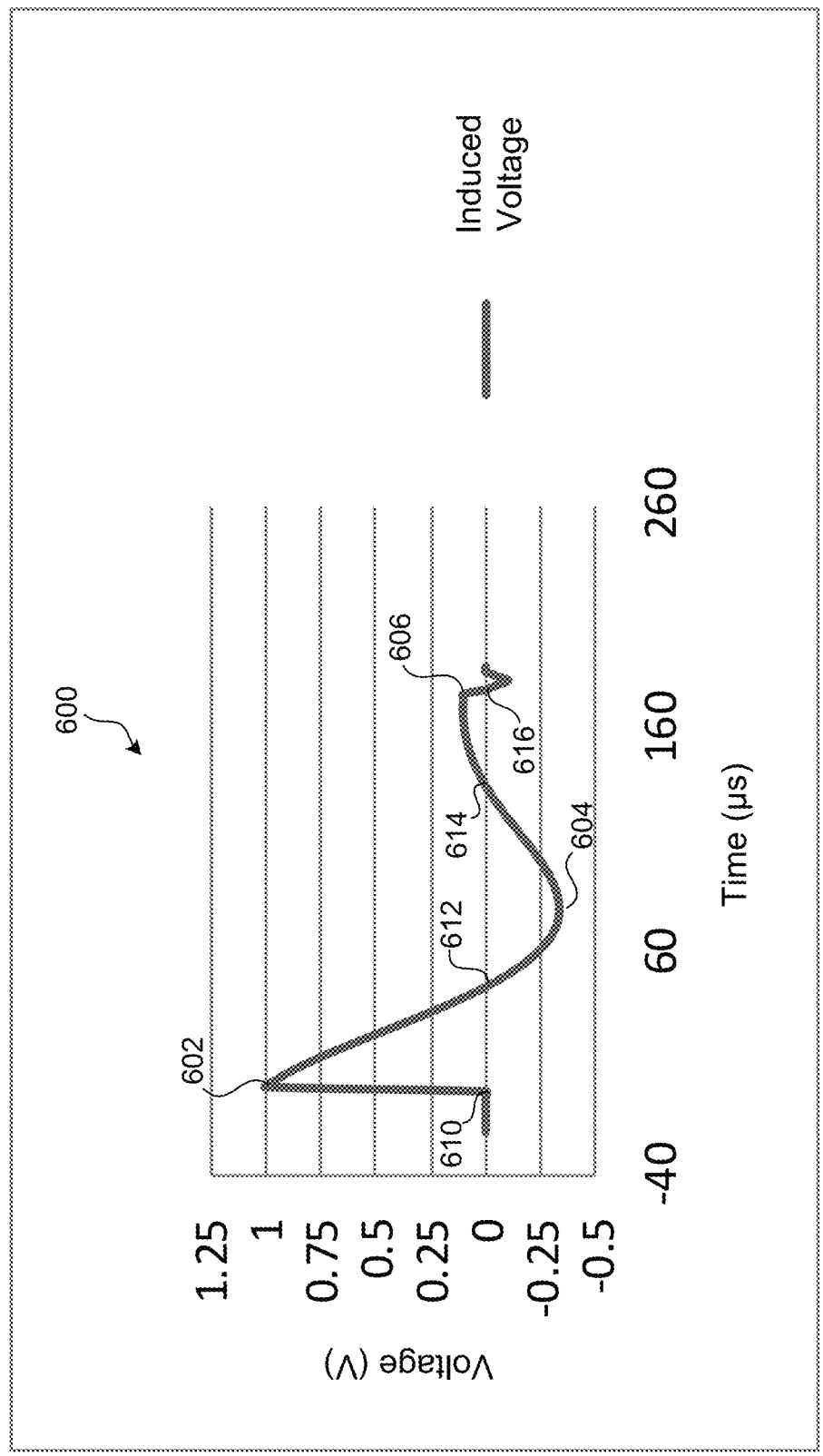
FIG. 6 is a diagram illustrating an example signal of a voltage induced on a sensor that is indicative of a failure.
Figure 7:
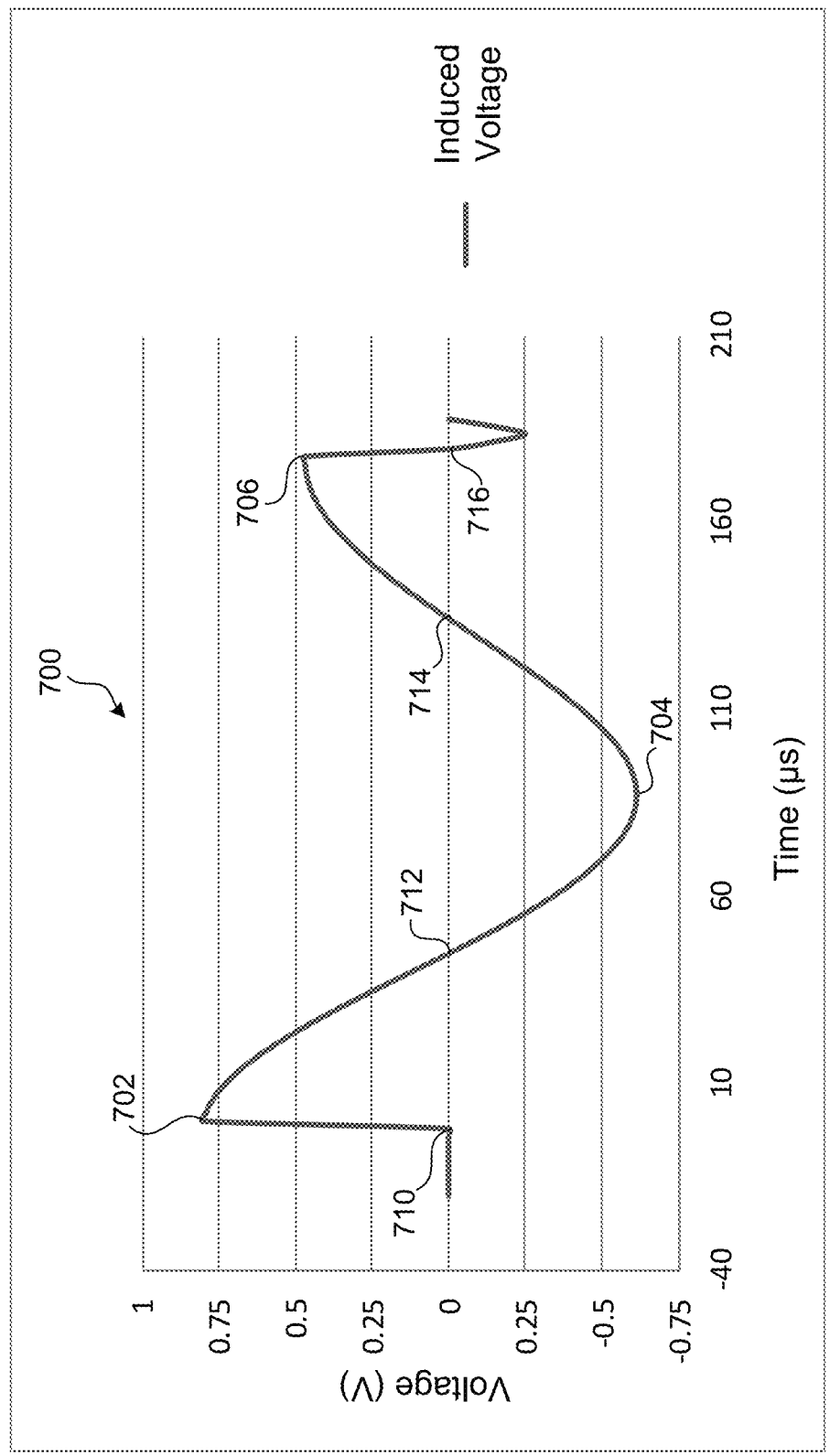
FIG. 7 is a diagram illustrating an example signal of a voltage induced on a sensor that is indicative of a failure.
Figure 8:
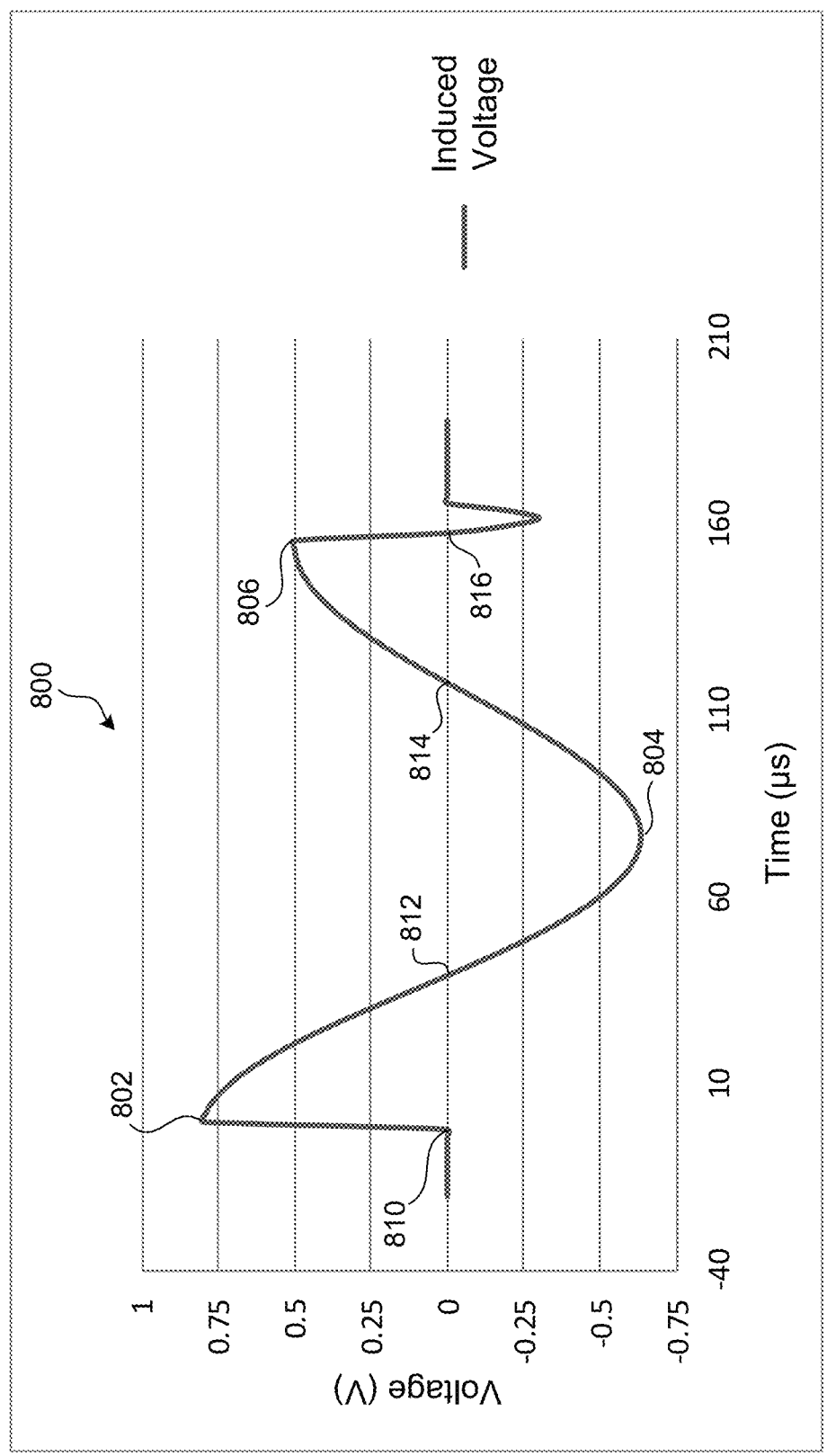
FIG. 8 is a diagram illustrating an example signal of a voltage induced on a sensor that is indicative of a failure.

FIGS. 5-8 are diagrams illustrating examples signals induced on a sensor of a magnetic stimulation system. As described herein, a magnetic stimulation system (e.g., magnetic stimulation system 100 or magnetic stimulation system 200) may be configured to determine whether a failure has occurred during a magnetic stimulation treatment or test session. The magnetic stimulation system may be configured to determine a wide variety of different failure types. Example signals associated with such failures may be provided herein, for example, with reference to FIGS. 6-8. The failures illustrated in FIGS. 6-8 are examples of the various types of signals that may be indicative of failures that may be detected by a magnetic stimulation system according to the one or more of the embodiments described herein. Further, the specific values associated with the signals of FIGS. 5-8 are examples and may be altered based on the specific magnetic stimulation treatment procedure being conducted, for example, in accordance with the settings of the magnetic stimulation procedure. The failure determinations described herein may be performed by a magnetic stimulation system (e.g., the magnetic stimulation system 100 or the magnetic stimulation system 200).

FIG. 5 is a diagram illustrating an example signal of an expected voltage generated by (e.g., induced on) a sensor. Although one pulse is illustrated in FIG. 5, the signal 500 may include one or more pulses of one or more pulse bursts. The signal 500 may be generated by a magnetic stimulation system (e.g., the magnetic stimulation system 100 or the magnetic stimulation system 200), for example, by a sensor of the magnetic stimulation system. The signal 500 may be provided to a controller of a magnetic stimulation system, for example, to determine whether a failure has occurred. The pulse of the signal 500 may include an initial rising edge 510, a first peak 502, a first zero-crossing 512, a second peak 504, a second zero-crossing 514, a third peak 506, and a third zero-crossing 516, for example, as described herein.

The signal 500 may be an expected voltage that is induced on the sensor. The magnetic stimulation system may utilize the signal 500 to determine whether a failure has occurred, for example, as described herein.

The signal 500 may include a pulse that is approximately 200 μs in length. The initial rising edge 510 may be at approximately time 0. The first peak 502 may be approximately 1 V and may occur approximately 5 μs after the initial rising edge 510. The first zero-crossing 512 may occur approximately 50 μs after the initial rising edge 510 about 45 μs after the first peak 502. The second peak 504 may be approximately −0.75 V and may occur approximately 80 μs after the initial rising edge 510 and approximately 30 μs after the first zero-crossing 512. The second zero-crossing 514 may occur approximately 130 μs after the initial rising edge 510 about 50 μs after the second peak 504. The third peak 506 may be approximately 0.6 V and may occur approximately 180 μs after the initial rising edge 510 and approximately 50 μs after the second zero-crossing 514. The third zero-crossing 516 may occur approximately 185 μs after the initial rising edge 510 about 5 μs after the third peak 506. The signal 500 may attenuate until settling at 0 V approximately 200 μs after the initial rising edge 510. As described herein, the signal 500 may include one or more pulses of one or more pulse bursts. A pulse of the signal 500 may look substantially similar to the pulse illustrated in FIG. 5.

FIG. 6 is a diagram illustrating an example signal of a voltage generated by (e.g., induced on) a sensor that is indicative of a failure. Although one pulse is illustrated in FIG. 6, the signal 600 may include one or more pulses of one or more pulse bursts. As shown, the pulse of the signal 600 may include an initial rising edge 610, a first peak 602, a first zero-crossing 612, a second peak 604, a second zero-crossing 614, a third peak 606, and a third zero-crossing 616, for example, as described herein. The first zero-crossing 612 may be referred to as a characteristic associated with the first peak 602, the second zero-crossing 614 may be referred to as a characteristic associated with the second peak 604, and/or the third zero-crossing 616 may be referred to as a characteristic associated with the third peak 606. An acceptance window may be adjustable based on the settings of the type of magnetic stimulation therapy, the magnetic stimulation treatment parameters, and/or the patient parameters. Failure detection may be performed during a test session, before magnetic stimulation therapy, and/or after magnetic stimulation therapy.

The magnetic stimulation system may detect a failure during a magnetic stimulation treatment session based on the decay rate of the pulsing magnetic field. For example, decay rate may refer to a rate at which a pulse associated with a pulsing magnetic field diminishes from the first peak to the last peak. Referring to FIG. 6, the signal 600 may be characterized by excessive loss. Excessive loss may be indicative of increased resistance of the magnetic stimulation system, which, for example, may be due to the failure of a connector and/or a switch of the magnetic stimulation system. The magnetic stimulation system may determine that a failure has occurred if the voltage ratio of the signal 600 is outside of a predetermined threshold, for example, a decay ratio acceptance window. The voltage ratio of the signal 600 may be the ratio between a voltage associated with two or more peaks of the signal 600, for example, a voltage associated with the first peak 602 and a voltage associated with the second peak 604.

For example, the magnetic stimulation system may determine that a failure has occurred if a voltage ratio of a generated signal (e.g., signal 600) is outside of a predetermined threshold. The magnetic stimulation system may estimate the voltage associated with two or more peaks of the generated signal (e.g., the first peak 602 and the second peak 604 of the pulse of the generated signal 600). The magnetic stimulation system may determine the voltage ratio of the generated signal using the voltage associated with the two or more peaks of the generated signal. For example, the voltage ratio may be a ratio of the voltage of a second peak (e.g., the second peak 604) to the voltage of a first peak (e.g., the first peak 602).

The magnetic stimulation system may determine if a failure has occurred using the voltage ratio, for example, by checking if the voltage ratio is outside of the decay ratio acceptance window. The decay ratio acceptance window may vary depending on one or more settings of the magnetic stimulation procedure. For example, the decay ratio acceptance window may be a range of the voltage ratio of the signal between a voltage value of a second peak (e.g., the second peak 604) and a voltage value of a first peak (e.g., the first peak 602). The decay ratio acceptance window may be a percentage (e.g., 10%), meaning that the voltage ratio of the signal may be plus/minus the percentage of the expected voltage ratio (e.g., as determined in accordance with the expected signal 500) to be within the decay ratio acceptance window. If the voltage is outside of the decay ratio acceptance window, then a failure may be determined to have occurred. For example, the decay ratio acceptance window may be between 0.6-1.0. For example, the decay ratio acceptance window may be between 0.65-0.95. For example, the decay ratio acceptance window may be between 0.65-0.85.

The magnetic stimulation system may determine that a failure has occurred if a voltage difference of two of the peaks of a signal (e.g., signal 600) generated by a sensor is outside of a predetermined threshold. The voltage difference may use the actual voltage values of the peaks or an absolute voltage value of the peaks. The voltage difference of the signal may be the voltage difference between a first peak and a second peak of the pulse of the generated signal (e.g., the first peak 602 and the second peak 604 of the signal 600). For example, the magnetic stimulation system may estimate the voltage associated with two or more peaks of the signal (e.g., the first peak and the second peak). The magnetic stimulation system may determine the voltage difference using the voltage associated with the two or more peaks (e.g., the voltage associated with the first peak and the voltage associated with the second peak).

The magnetic stimulation system may determine if a failure has occurred using the voltage difference, for example, by checking if the voltage difference is outside of the peak-to-peak acceptance window. For example, the peak-to-peak acceptance window may be 10%, meaning that the voltage difference of the signal may be plus/minus 10% of the expected voltage difference (e.g., as determined in accordance with the expected signal 500) to be within the peak-to-peak acceptance window. For example, the peak-to-peak acceptance window may be between 1.3-2.2 V if absolute values of the voltage peaks are used. For example, the peak-to-peak acceptance window may be between 1.45-2.5 V if absolute values of the voltage peaks are used. For example, the peak-to-peak acceptance window may be between 1.6-1.9 V, if absolute values of the voltage peaks are used. Further, the peak-to-peak acceptance window may be dependent upon the size of the sensor, for example, if the sensor is a pickup loop.

FIG. 7 is a diagram illustrating another example waveform of a voltage generated by (e.g., induced on) a sensor during a magnetic stimulation treatment that is indicative of a failure. Although one pulse is illustrated in FIG. 7, the signal 700 may include one or more pulses of one or more pulse bursts. As shown, the pulse of the signal 700 may include an initial rising edge 710, a first peak 702, a first zero-crossing 712, a second peak 704, a second zero-crossing 714, a third peak 706, and a third zero-crossing 716, for example, as described herein. The first zero-crossing 712 may be referred to as a characteristic associated with the first peak 702, the second zero-crossing 714 may be referred to as a characteristic associated with the second peak 704, and/or the third zero-crossing 716 may be referred to as a characteristic associated with the third peak 706. An acceptance window may be adjustable based on the settings of the type of magnetic stimulation therapy, the magnetic stimulation treatment parameters, and/or the patient parameters. Failure detection may be performed during a test session, before magnetic stimulation therapy, and/or after magnetic stimulation therapy.

The magnetic stimulation system may detect a failure based on the amplitude of a peak of the pulsing magnetic field. For example, the amplitude of a peak may refer to the maximum or minimum voltage and/or current associated with the peak. The signal 700 may be characterized by smaller peak voltages. Smaller peak voltages, for example, as illustrated by signal 700, may be indicative of a failure that reduces the capacitor charge and/or the voltage applied to the magnetic stimulation component by the magnetic stimulation system. For example, a signal 700 may be received if a power supply, connector, thyrister, shunt device, wiring, and/or the like of the magnetic stimulation system had failed or begun to fail. The magnetic stimulation system may determine that a failure has occurred if an amplitude (e.g., voltage or current) associated with a peak of the signal 700 is outside of a predetermined threshold, for example, an amplitude acceptance window. For example, the amplitude of a peak of the signal 700 may refer to the voltage at the first peak 702, the second peak 704, and/or the third peak 706.

The magnetic stimulation system may determine that a failure has occurred if an amplitude of a voltage associated with a peak of a generated signal (e.g., signal 700) is outside of a predetermined threshold. The magnetic stimulation system may estimate an initial rising edge (e.g., an initial rising edge 710) and/or a zero-crossing (e.g., zero-crossing 712, 714, 716) associated with one or more peaks of the generated signal (e.g., the first peak 702, the second peak 704, and/or the third peak 706 of the pulse of the generated signal). For example, the magnetic stimulation system may determine a voltage associated with the first peak, a voltage associated with the second peak, and/or a voltage associated with the third peak of the generated signal using the initial rising edge and/or the zero-crossing associated with the one or more peaks of the generated signal.

For example, the magnetic stimulation system may determine if a failure has occurred using the amplitude of one or more peaks of the signal, for example, by checking if the amplitude is outside of the amplitude acceptance window. For example, the amplitude acceptance window may be 10%, meaning that the amplitude of a peak of the signal may be plus/minus 10% of the expected amplitude of a peak (e.g., as determined in accordance with the expected signal 500) to be within the amplitude acceptance window. For example, the amplitude acceptance window may be between 0.7-1.3 V for a first peak of a pulse of a generated signal. For example, the amplitude acceptance window may be between 0.8-1.2 V for a first peak of a pulse of a generated signal. For example, the amplitude acceptance window may be between 0.9-1.1 V for a first peak of a pulse of a generated signal.

The magnetic stimulation system may determine that a failure has occurred if an average amplitude of two or more peaks (e.g., first peak 702, second peak 704, and/or third peak 706) of a pulse(s) of a generated signal (e.g., signal 700) is outside of a predetermined threshold. The magnetic stimulation system may estimate a voltage associated with two or more peaks of a pulse(s) of the generated signal. The magnetic stimulation system may determine an average voltage amplitude of two or more peaks of the generated signal using the voltage associated with the two or more peaks of the generated signal.

For example, the magnetic stimulation system may determine if a failure has occurred using the average voltage amplitude, for example, by checking if the average voltage amplitude is outside of an average amplitude acceptance window. For example, the average amplitude acceptance window may be 10%, meaning that the average amplitude of two or more peaks of a pulse(s) of the signal may be plus/minus 10% of the expected average amplitude (e.g., as determined in accordance with the expected signal 500) to be within the average amplitude acceptance window. For example, the average amplitude acceptance window may be between 1.25-1.95 V for a first peak and a third peak of a pulse of a generated signal. For example, the average amplitude acceptance window may be between 1.4-1.8 V for a first peak and a third peak of a pulse of a generated signal. For example, the average amplitude acceptance window may be between 1.5-1.7 V for a first peak and a third of a pulse of a generated signal.

The magnetic stimulation system may detect a failure based on the pulse shape and/or the peak to RMS voltage ratio of the pulsing magnetic field. The signal 700 may be characterized by a smaller peak to RMS ratio. For example, peak to RMS ratio may be the ratio of a peak voltage (e.g., the voltage associated with the first peak 702) to the RMS value of a peak of the signal 700. Smaller peak to RMS ratio value, for example, as illustrated by signal 700, may be indicative of a failure that reduces the capacitor charge and/or the voltage applied to the magnetic stimulation component by the magnetic stimulation system.

The magnetic stimulation system may determine that a failure has occurred if a ratio between a peak (e.g., the first peak) of a pulse of a generated signal (e.g., signal 700) and a peak to RMS voltage ratio is outside of a predetermined threshold. The magnetic stimulation system may estimate a voltage and/or a time associated with one or more peaks of a pulse(s) of the generated signal. The magnetic stimulation system may determine a peak to RMS voltage ratio of the generated signal using the voltage and/or time associated with the one or more peaks of a pulse(s) of the generated signal.

For example, the magnetic stimulation system may determine if a failure has occurred using the peak to RMS voltage ratio, for example, by checking if the ratio between the voltage of the peak and the peak to RMS voltage ratio is outside of the peak to RMS voltage acceptance window. For example, the peak to RMS voltage acceptance window may be 10%, meaning that the ratio between the voltage of the peak and the peak to RMS voltage ratio may be plus/minus 10% of what is expected (e.g., as determined in accordance with the expected signal 500) to be within the peak to RMS voltage acceptance window. For example, the peak to RMS voltage acceptance window may be between 1.15-1.65. For example, the peak to RMS voltage acceptance window may be between 1.25-1.55. For example, the peak to RMS voltage acceptance window may be between 1.3-1.5.

Pulse shape may refer to the shape of a pulse of the pulsing magnetic field. The peak to RMS ratio is one example of how a shape of the generated signal may be used by a magnetic stimulation system to determine whether a failure has occurred. Other examples may be provided herein. For example, characteristics of a generated signal, such as duration, skewness, kurtosis, among others, may relate to the shape of the generated signal and may be used to determine whether a failure has occurred. The magnetic stimulation system may determine that a failure has occurred if a shape of a generated signal is outside of a predetermined acceptance window. The magnetic stimulation system may be configured to estimate a pulse shape, a pulse time, a pulse amplitude, and/or a pulse duration associated with one or more peaks of a pulse(s) of a generated signal. The magnetic stimulation system may be configured to determine one or more characteristics based on the one or more estimated characteristics of the generated signal. The magnetic stimulation system may determine that a failure has occurred when the one or more determined characteristics are outside of a predetermined acceptance window, for example, a pulse shape acceptance window.

Skewness of the generated signal, for example, may be used determine if a failure has occurred. The magnetic stimulation system may estimate the voltage and/or time of one or more peaks of a pulse(s) of the generated signal, the magnetic stimulation system may determine the voltage per time of the generated signal (e.g., which may be indicative of the skewness of a pulse of the generated signal), and the magnetic stimulation system may determine if a failure has occurred by determining if the voltage per time of the generated signal falls within a skewness acceptance window.

FIG. 8 is a diagram illustrating an example waveform of a voltage generated by (e.g., induced on) a sensor during magnetic stimulation that is indicative of a failure. Although one pulse is illustrated in FIG. 8, the signal 800 may include one or more pulses of one or more pulse bursts. As shown, the pulse of the signal 800 may include an initial rising edge 810, a first peak 802, a first zero-crossing 812, a second peak 804, a second zero-crossing 814, a third peak 806, and a third zero-crossing 816, for example, as described herein. An acceptance window may be adjustable based on the settings of the type of magnetic stimulation therapy, the magnetic stimulation treatment parameters, and/or the patient parameters. Failure detection may be performed during a test session, before magnetic stimulation therapy, and/or after magnetic stimulation therapy.

The magnetic stimulation system may detect a failure based on the pulse duration of the pulsing magnetic field. The time duration between the initial rising edge 810 and the third zero-crossing 816 of the signal 800 may be referred to as the pulse duration of the signal 800. The signal 800 may be characterized by a shorter pulse duration than the expected signal 500. A shorter pulse duration, for example, as illustrated by signal 800, may be indicative of a failing capacitor, a shorted winding (e.g., in the core), a broken core, and/or the like.

The magnetic stimulation system may determine whether a failure has occurred based on the pulse duration of a generated signal. For example, the pulse duration may refer to the time duration between the initial rising edge of a pulse and the third zero-cross of the pulse. For example, the pulse duration may refer to the time duration between the initial rising edge of a pulse and the third peak of the pulse. For example, the pulse duration may refer to the time duration between the first peak of a pulse and the third peak of a pulse. For example, the pulse duration may refer to the time duration between the first zero-crossing and the second zero-crossing. For example, the pulse duration may be characterized by two zero-crossings of a pulse, the width of a pulse, or the like.

The magnetic stimulation system may be configured to estimate a time associated with two or more peaks of a pulse(s) of a generated signal (e.g., the first peak, the second peak, and/or the third peak of a pulse of a generated signal). For example, the magnetic stimulation system may estimate a time associated with a first peak and a third peak associated with a single pulse of a generated signal (e.g., the first peak 802 and the third peak 806 as shown in FIG. 8). For example, the magnetic stimulation system may estimate a time associated with a first peak and a time associated with a second peak of a generated signal. The magnetic stimulation system may determine a pulse duration of the generated signal based on the time duration associated with the two or more peaks associated with the same pulse of the generated signal.

The magnetic stimulation system may determine if a failure has occurred based on the pulse duration, for example, by checking if the pulse duration is outside of a pulse duration acceptance window. The pulse duration acceptance window may be adjustable based on the settings of the type of magnetic stimulation therapy, the magnetic stimulation treatment parameters, and/or the patient parameters. For example, the pulse duration acceptance window may be 10%, meaning that the pulse duration of the signal may be plus/minus 10% of the expected pulse duration (e.g., as determined in accordance with the expected signal 500) to be within the pulse duration acceptance window. For example, the pulse duration acceptance window may be between 300-350 μs. For example, the pulse duration acceptance window may be between 175-275 μs. For example, the pulse duration acceptance window may be between 200-250 μs.

The magnetic stimulation system may determine whether a failure has occurred based on an average pulse duration of a generated signal (e.g., signal 800). The magnetic stimulation system may estimate a time associated with two or more peaks of a pulse(s) of the generated signal. The two or more peaks may be associated with different pulses of the generated signal. The magnetic stimulation system may determine an average pulse duration of the two or more pulses of the generated signal using the time associated with the two or more peaks of a pulse(s) of the generated signal. For example, the magnetic stimulation system may determine the pulse durations of two or more pulses of the generated signal, and using the pulse durations of two or more pulses, the magnetic stimulation system may calculate an average pulse duration of the generated signal.

The magnetic stimulation system may determine if a failure has occurred using the average pulse duration, for example, by checking if the average pulse duration is outside of the average pulse duration acceptance window. For example, the average pulse duration acceptance window may be 10%, meaning that the average pulse duration of the signal may be plus/minus 10% of the expected average pulse duration (e.g., as determined in accordance with the expected signal 500) to be within the average pulse duration acceptance window. For example, the average pulse duration acceptance window may be between 150-250 μs. For example, the average pulse duration acceptance window may be between 175-225 μs. For example, the average pulse duration acceptance window may be between 190-210 μs.

The magnetic stimulation system may determine whether a failure has occurred based on a sum of the pulse durations of a signal (e.g., signal 800) generated by a sensor. The magnetic stimulation system may estimate a time associated with two or more peaks of a pulse(s) of the generated signal. The two or more peaks may be associated with different pulses of the generated signal. The magnetic stimulation system may determine a sum of the pulse durations of the two or more pulses of the generated signal using the time associated with the two or more peaks of the generated signal.

The magnetic stimulation system may determine if a failure has occurred using the sum of the pulse durations, for example, by checking if the sum of the pulse durations is outside of the pulse duration sum acceptance window. For example, the pulse duration sum acceptance window may be 10%, meaning that the sum of pulses of the signal may be plus/minus 10% of the expected pulse duration sum (e.g., as determined in accordance with the expected signal 500) to be within the pulse duration sum acceptance window. For example, the pulse duration sum acceptance window may be between 300-500 μs for two pulses of a generated signal. For example, the pulse duration sum acceptance window may be between 350-450 μs for two pulses of a generated signal. For example, the pulse duration sum acceptance window may be between 380-420 μs for two pulses of a generated signal.

The magnetic stimulation system may detect a failure based on the stimulation time duration of the pulsing magnetic field. The magnetic stimulation system may determine whether a failure has occurred based on the stimulation time duration of a signal generated by a sensor. As described herein, the stimulation time duration of a generated signal may refer to the time between a first peak of a first pulse of a pulse burst and a first peak of a last pulse of the pulse burst of the signal. The magnetic stimulation system may estimate a time associated with a peak (e.g., the first peak) of a first pulse of a pulse burst and a time associated with a peak (e.g., the first peak) of a last pulse of the pulse burst. The magnetic stimulation system may determine the stimulation time of the pulse burst of the generated signal using the time associated with the peak of the first pulse of the pulse burst and the time associated with the peak of the last pulse of the pulse burst of the signal.

The magnetic stimulation system may determine if a failure has occurred using the stimulation time, for example, by checking if the stimulation time is outside of a stimulation time acceptance window. For example, the stimulation time acceptance window may be 10%, meaning that the stimulation time of the signal may be plus/minus 10% of the expected stimulation time (e.g., as determined in accordance with the expected signal 500) to be within the stimulation time acceptance window. For example, the stimulation time acceptance window may be between 3.5-4.5 s. For example, the stimulation time acceptance window may be between 3.9-4.1 s. For example, the stimulation time acceptance window may be between 3.95-4.05 s.

The magnetic stimulation system may detect a failure based on the pulse interval of the pulsing magnetic field. The magnetic stimulation system may determine whether a failure has occurred based on the pulse interval of a generated signal. As described herein, the pulse interval of a generated signal may refer to the time duration between a first peak of a pulse of a generated signal and a first peak of a subsequent pulse (e.g., immediately subsequent pulse) of the signal. For example, the pulse interval of a generated signal may refer to the number of pulses per second associated with the pulsing magnetic field.

For example, the magnetic stimulation system may estimate a time associated with a peak (e.g., the first peak) of a pulse of the generated signal and a time associated with a peak (e.g., the first peak) of a subsequent pulse of the generated signal. For example, the pulse and the subsequent pulse may be consecutive pulses in a pulse burst of the generated signal. The magnetic stimulation system may determine the pulse interval of the generated signal using the time associated with the peak of the pulse of the generated signal and a time associated with the peak of the subsequent pulse of the generated signal.

The magnetic stimulation system may determine if a failure has occurred using the pulse interval, for example, by checking if the pulse interval is outside of a pulse interval acceptance window. For example, the pulse interval acceptance window may be 10%, meaning that the pulse interval of the signal may be plus/minus 10% of the expected pulse interval (e.g., as determined in accordance with the expected signal 500) to be within the pulse interval acceptance window. For example, the pulse interval acceptance window may be between 225-475 µs. For example, the pulse interval acceptance window may be between 250-450 µs. For example, the pulse interval acceptance window may be between 300-400 µs.

The magnetic stimulation system may detect a failure based on the stimulation interval of the pulsing magnetic field. The magnetic stimulation system may determine whether a failure has occurred based on the stimulation interval of a signal generated by a sensor. As described herein, the stimulation interval of a generated signal may be indicative of the time duration between a first peak of a last pulse of a pulse burst and a first peak of a first pulse of a subsequent (e.g., immediate subsequent) pulse burst of the signal. The magnetic stimulation system may estimate a time associated with a peak (e.g., the first peak) of a last pulse of a pulse burst and a time associated with a peak (e.g., the first peak) of a first pulse of a subsequent pulse burst. For example, the pulse burst and the subsequent pulse burst may be consecutive pulse bursts of the generated signal. The magnetic stimulation system may determine the stimulation interval of the generated signal using the time associated with the peak of the first pulse of the pulse burst and the time associated with the peak of the first pulse of the subsequent pulse burst of the signal.

The magnetic stimulation system may determine if a failure has occurred using the stimulation interval, for example, by checking if the stimulation interval is outside of a stimulation interval acceptance window. For example, the stimulation interval acceptance window may be 10%, meaning that the stimulation interval of the signal may be plus/minus 10% of the expected stimulation interval (e.g., as determined in accordance with the expected signal 500) to be within the stimulation interval acceptance window. For example, the stimulation interval acceptance window may be between 3-17 s. For example, the stimulation interval acceptance window may be between 6-14 s. For example, the stimulation interval acceptance window may be between 9-10 s.

The magnetic stimulation system may detect a failure based on the pulse repetition rate of the pulsing magnetic field. The magnetic stimulation system may determine whether a failure has occurred based on the pulse repetition rate of a signal generated by a sensor. As described herein, the pulse repetition rate of a generated signal may be indicative of the number of pulses per time duration (e.g., pulses per second (pps)). The magnetic stimulation system may estimate times associated with a number of peaks over a predefined period of time (e.g., one second) to determine the pulse repetition rate of a generated signal.

The magnetic stimulation system may determine if a failure has occurred using the pulse repetition rate, for example, by checking if the pulse repetition rate is outside of a pulse repetition rate acceptance window. For example, the pulse repetition rate acceptance window may be 10%, meaning that the pulse repetition rate of the signal may be plus/minus 10% of the expected pulse repetition rate (e.g., as determined in accordance with the expected signal 500) to be within the pulse repetition rate acceptance window. For example, the pulse repetition rate acceptance window may be between 3-40 pps. For example, the stimulation interval acceptance window may be between 5-30 pps. For example, the stimulation interval acceptance window may be between 10-20 pps.

The magnetic stimulation system may detect a failure by measuring and/or estimating a rolling average value and/or a weighted average value of a generated signal associated with a pulsing magnetic field. For example, the magnetic stimulation system may determine that a failure has occurred if the rolling average and/or a weighted average one or more pulse sets deviate by more than a threshold or percentage. The threshold or percentage may be predetermined, fixed, and/or adjustable. For example, the threshold or percentage may be adjustable based on the settings of the type of magnetic stimulation therapy, the magnetic stimulation treatment parameters, and/or the patient parameters. The magnetic stimulation system may take larger samples of the pulsing magnetic field and detect the failure over a greater sample size than using just one or two peaks of a pulse of the pulsing magnetic field.

As described herein, the magnetic stimulation system may include a magnetic stimulation component that may generate a pulsing magnetic field for a magnetic stimulation procedure. The magnetic stimulation system may estimate average values for pulse sets of the generated signal. For example, an average value for a corresponding set of pulses may be an average maximum voltage of the set of pulses, an average minimum voltage of the set of pulses, an average time duration of the set pulses, an average time per pulse of the set of pulses, and/or an average decay rate per pulse of the set of pulses. For example, an average value for a corresponding pulse set may include an average maximum voltage of one or more peaks of the pulses of the pulse set, or the like. The average values may be weighted averages or unweighted averages.

For example, two average values of two pulse sets may be estimated. The first average value may be associated with a first set of pulses of the pulsing magnetic field. The first set of pulses of the pulsing magnetic field may include two or more pulses, which may or may not be part of the same pulse burst of the pulsing magnetic field. The second average value may be associated with a second set of pulses of the pulsing magnetic field. The second set of pulses of the pulsing magnetic field may include two or more pulses, which may or may not be part of the same pulse burst of the pulsing magnetic field. The first set of pulses and the second set of pulses may be associated with the same pulse burst of different pulse bursts of the pulsing magnetic field. The first set of pulses and the second set of pulses may include one or more of the same pulses. The first average value and the second average value may or may not relate to the same characteristic of the generated signal. Although described with reference to a first and second average value, the magnetic stimulation system may utilize any number of average values to determine a failure associated with a pulsing magnetic field.

The magnetic stimulation system may determine whether a failure occurred based on the estimated first average value and the estimated second average value. For example, the failure may be determined to have occurred when the first average value and the second average value deviate by more than a threshold or percentage. For example, the failure may be determined to have occurred when the first average value and the second average value deviate by more than a rolling average acceptance window (e.g., which may be 10%).

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

What is claimed is:

1. A system for monitoring a pulsing magnetic field related to magnetic stimulation therapy, the system comprising:
   a magnetic stimulation component configured to generate the pulsing magnetic field for the magnetic stimulation therapy;
   a sensor configured to generate a signal in response to the pulsing magnetic field; and
   a processor configured to:
      generate a pulse burst of the pulsing magnetic field by driving the magnetic stimulation component;
      receive a signal from the sensor in response to the pulse burst of the magnetic stimulation component, wherein the signal comprises a plurality of pulses, and wherein each pulse of the signal comprises a plurality of peaks, and each pulse of the signal was generated in response to a pulse of the pulse burst;
      estimate a characteristic of a first peak for two or more pulses of the pulse burst;
      determine that a failure has occurred based on the characteristic of the first peak across the two or more pulses of the pulse burst; and
      perform at least one action based on the determination that a failure has occurred, the at least one action comprising one or more of shutting down the system, stopping the magnetic stimulation therapy, alerting a user of the system, or altering a current applied to the magnetic stimulation component.

2. The system of claim 1, wherein the processor is configured to estimate the characteristic of the first peak for the two or more pulses by determining one or more of a rolling average value or a weighted average value for the characteristic of the first peak across the two or more pulses.

3. The system of claim 1, wherein the characteristic comprises a maximum amplitude of the first peak; and
   wherein the processor is configured to determine an average maximum amplitude of the two or more pulses of the pulse burst, and determine that the failure occurred when the average maximum amplitude is outside of an amplitude acceptance window.

4. The system of claim 1, wherein the characteristic comprises a time value of the first peak; and
   wherein the processor is configured to determine a pulse interval based a time difference between a time value of the first peak of a first pulse of the plurality of pulses and a time value of the first peak of a subsequent pulse of the plurality of pulses, and determine that the failure occurred when the pulse interval is outside of a pulse interval acceptance window.

5. The system of claim 1, wherein the characteristic comprises a time value of the first peak; and
   wherein the processor is configured to determine a stimulation time of the pulse burst based a time difference between a time value of the first peak of a first pulse of the plurality of pulses and a time value of the first peak of a last pulse of the plurality of pulses, and determine that the failure occurred when the stimulation time of the pulse burst is outside of a stimulation time acceptance window.

6. The system of claim 1, wherein the processor is configured to estimate a characteristic of a second peak for the two or more pulses of the pulse burst, and determine that the failure has occurred based on the characteristic of the first peak and the characteristic of the second peak across the two or more pulses of the pulse burst.

7. The system of claim 6, wherein the characteristic of the first peak comprises a voltage or current value of the first peak, and the characteristic of the second peak comprises a voltage or current value of the second peak.

8. The system of claim 7, wherein the processor is configured to determine a decay rate of the pulse burst based on a ratio between the voltage or current value of the first peak and the voltage or current value of the second peak, and determine that the failure has occurred when the ratio is outside of a ratio acceptance window.

9. The system of claim 7, wherein the processor is configured to determine a difference between the peaks of the two or more pulses of the pulse burst based on a difference between the voltage or current value of the first peak and the voltage or current value of the second peak, and determine that the failure has occurred when the difference is outside of a peak-to-peak acceptance window.

10. The system of claim 7, wherein the characteristic of the first peak comprises a time value of the first peak, and the characteristic of the second peak comprises a time value of the second peak; and
    wherein the processor is configured to determine a pulse duration of the two or more pulses of the pulse burst based on a difference between the time value of the first peak and the time value of the second peak, and determine that the failure has occurred when the pulse duration is outside of a pulse duration acceptance window.

11. The system of claim 1, wherein the pulse burst of the pulsing magnetic field comprises one or more test pulses, and wherein the pulse burst is generated as part of a test procedure.

12. The system of claim 11, wherein the processor is further configured to:
    perform a treatment procedure using the magnetic stimulation component, wherein the treatment procedure is performed subsequent to the test procedure.

13. A system for monitoring a pulsing magnetic field related to magnetic stimulation therapy, the system comprising:
    a magnetic stimulation component configured to generate the pulsing magnetic field for the magnetic stimulation therapy;
    a sensor configured to generate a signal in response to the pulsing magnetic field; and
    a processor configured to:
       generate a first pulse burst of the pulsing magnetic field by driving the magnetic stimulation component at a first drive level, and a second pulse burst of the pulsing magnetic field by driving the magnetic stimulation component at a second drive level;

receive a first signal from the sensor in response to the first pulse burst and a second signal from the sensor in response to the second pulse burst, wherein each of the first and second signals comprises a plurality of pulses, and wherein each pulse of the first and second signal comprises a plurality of peaks, and each pulse of the first and second signal was generated in response to a pulse of either the first or second pulse burst;

determine one or more of a rolling average value or a weighted average value for a characteristic of a first peak for each of the pulses of the first pulse burst;

determine one or more of a rolling average value or a weighted average value for a characteristic of the first peak for each of the pulses of the second pulse burst;

determine that a failure has occurred based on the characteristic of the first peak for each of the pulses of the first pulse burst or the characteristic of the first peak for each of the pulses of the second pulse burst; and perform at least one action based on the determination that a failure has occurred, the at least one action comprising one or more of shutting down the system, stopping the magnetic stimulation therapy, alerting a user of the system, or altering a current applied to the magnetic stimulation component.

14. The system of claim 13, wherein the processor is configured to:

determine one or more of a rolling average value or a weighted average value for the characteristic of a second peak for each of the pulses of the first pulse burst;

determine one or more of a rolling average value or a weighted average value for a characteristic of the second peak for each of the pulses of the second pulse burst;

determine that a failure has occurred based on the characteristics of the first and second peaks for each of the pulses of the first pulse burst or the characteristics of the first and second peaks for each of the pulses of the second pulse burst.

15. The system of claim 13, wherein the first pulse burst of the pulsing magnetic field comprises a first set of one or more test pulses and the second pulse burst of the pulsing magnetic field comprises a second set of one or more test pulses, and wherein the first pulse burst and the second pulse burst are generated as part of a test procedure.

16. The system of claim 15, wherein the processor is further configured to:

perform a treatment procedure using the magnetic stimulation component, wherein the treatment procedure is performed subsequent to the test procedure.

17. A system for monitoring a pulsing magnetic field related to magnetic stimulation therapy, the system comprising:

a magnetic stimulation component configured to generate the pulsing magnetic field for the magnetic stimulation therapy;

a sensor configured to generate a signal in response to the pulsing magnetic field, the signal comprising at least one pulse, wherein each pulse of the signal is associated with a pulse of the pulsing magnetic field, and each pulse of the signal comprises a plurality of peaks; and a processor configured to:

estimate a characteristic of a first peak for each pulse across a first set of pulses of the signal;

estimate a characteristic of a second peak for each pulse across a second set of pulses of the signal;

determine that a failure has occurred based on a comparison of the characteristic of the first peak and the characteristic of the second peak; and perform at least one action based on the determination that a failure has occurred, the at least one action comprising one or more of shutting down the system, stopping the magnetic stimulation therapy, alerting a user of the system, or altering a current applied to the magnetic stimulation component.

18. The system of claim 17, wherein the characteristic of the first peak comprises a voltage of the first peak, a current of the first peak, an RMS value of the first peak, a zero-cross of the first peak, a time value of the first peak, or a time duration of the first peak, and wherein the characteristic of the second peak comprises a voltage of the second peak, a current of the second peak, an RMS value of the second peak, a zero-cross of the second peak, a time value of the second peak, or a time duration of the second peak.

19. The system of claim 17, wherein the processor is configured to determine one or more of a rolling average value or a weighted average value for the characteristic of the first peak across the first set of pulses to estimate the characteristic of the first peak; and wherein the processor is configured to determine one or more of a rolling average value or a weighted average value for the characteristic of the second peak across the second set of pulses to estimate the characteristic of the second peak.

20. The system of claim 17, wherein the first and second sets of pulses are the same.

21. The system of claim 20, wherein the first peak is characterized by a first positive voltage of each pulse of the first and second sets of pulses and the second peak is characterized by a second positive voltage of each pulse of the first and second sets of pulses, and wherein the failure is determined to have occurred when the time between the first peak and the second peak is outside of a pulse duration acceptance window.

22. The system of claim 17, wherein the first set of pulses is different from the second sets of pulses.

23. The system of claim 17, wherein the failure is determined to have occurred when a voltage ratio between the characteristic of the first peak and the characteristic of the second peak is outside of a decay ratio acceptance window; or wherein the failure is determined to have occurred when a voltage difference between the characteristic of the first peak and the characteristic of the second peak is outside of a peak-to-peak acceptance window.

24. The system of claim 17, wherein the first and second sets of pulses are different; and wherein the first peak is associated with a first pulse of a pulse burst of the pulsing magnetic field and the second peak is associated with a second pulse of the pulse burst of the pulsing magnetic field and wherein the failure is determined to have occurred when a time duration between the first peak and the second peak of each pulse burst of the set of pulses is outside of a pulse interval acceptance window; or wherein the first peak is associated with a last pulse of a first pulse burst of the pulsing magnetic field and the second peak is associated with a first pulse of a second pulse burst of the pulsing magnetic field, wherein the first pulse burst and the second pulse burst are consecutive pulse bursts, and wherein the failure is determined to have occurred when a time duration between the first peak and the second peak of each consecutive pulse bursts of the set of pulses is outside of a stimulation interval acceptance window.

25. The system of claim 17, wherein the pulse of the pulsing magnetic field is a test pulse, and wherein the pulsing magnetic field is generated as part of a test procedure.

26. The system of claim 25, wherein the processor is further configured to:
perform a treatment procedure using the magnetic stimulation component, wherein the treatment procedure is performed subsequent to the test procedure.

* * * * *